(12) United States Patent
Purdie et al.

(10) Patent No.: US 9,421,397 B2
(45) Date of Patent: Aug. 23, 2016

(54) METHODS AND SYSTEMS FOR AUTOMATED PLANNING OF RADIATION THERAPY

(75) Inventors: Thomas G. Purdie, Oakville (CA); Michael B. Sharpe, Mississauga (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 597 days.

(21) Appl. No.: 13/877,754

(22) PCT Filed: Oct. 6, 2011

(86) PCT No.: PCT/CA2011/001130
§ 371 (c)(1),
(2), (4) Date: Jun. 18, 2013

(87) PCT Pub. No.: WO2012/045163
PCT Pub. Date: Apr. 12, 2012

(65) Prior Publication Data
US 2013/0289332 A1    Oct. 31, 2013

Related U.S. Application Data

(60) Provisional application No. 61/390,376, filed on Oct. 6, 2010.

(51) Int. Cl.
*A61N 5/10* (2006.01)

(52) U.S. Cl.
CPC .............. *A61N 5/1039* (2013.01); *A61N 5/103* (2013.01); *A61N 5/1045* (2013.01); *A61N 2005/1041* (2013.01); *A61N 2005/1074* (2013.01)

(58) Field of Classification Search
CPC .. A61N 5/1049; A61N 5/1037; A61N 5/1038
USPC ................................................ 600/1; 378/65
See application file for complete search history.

(56) References Cited

U.S. PATENT DOCUMENTS

| | | |
|---|---|---|
| 2004/0165696 A1 | 8/2004 | Lee |
| 2005/0101860 A1* | 5/2005 | Patrick ................. A61N 5/1049 600/433 |
| 2006/0293583 A1* | 12/2006 | Saracen ............... A61N 5/1038 600/407 |
| 2007/0088573 A1 | 4/2007 | Ruchala et al. |
| 2009/0262894 A1 | 10/2009 | Shukla et al. |
| 2010/0208867 A1 | 8/2010 | Nord et al. |

FOREIGN PATENT DOCUMENTS

WO    2007014106 A2    2/2007

OTHER PUBLICATIONS

Kestin L.L., Sharpe M.B., Frazier R.C., et al., Intensity modulation to improve dose uniformity with tangential breast radiotherapy: initial clinical experience, Int. J. Radiation Oncology Biol. Phys., 2000, vol. 48, pp. 1559-1568.

(Continued)

*Primary Examiner* — Samuel Gilbert
(74) *Attorney, Agent, or Firm* — Norton Rose Fulbright Canada LLP

(57) ABSTRACT

Methods and systems for automated treatment planning for radiation therapy are disclosed. Such methods and systems may be useful for treatment planning for intensity-modulate radiotherapy (IMRT). Also provided are user interfaces for automated radiation therapy treatment planning.

34 Claims, 21 Drawing Sheets

(56) References Cited

OTHER PUBLICATIONS

Vicini F.A., Sharpe M., Kestin L., et al., Optimizing breast cancer treatment efficacy with intensitymodulated radiotherapy, Int. J. Radiation Oncology Biol. Phys., 2002, vol. 54, pp. 1336-1344.

Harsolia A., Kestin L., Grills I., et al., Intensity-modulated radiotherapy results in significant decrease in clinical toxicities compared with conventional wedge-based breast radiotherapy, Int. J. Radiation Oncology Biol. Phys., 2007, vol. 68, pp. 1375-1380.

Pignol J.P., Olivotto I., Rakovitch E., et al. A multicenter randomized trial of breast intensity-modulated radiation therapy to reduce acute radiation dermatitis. Journal of Clinical Oncology, 2008, vol. 26, pp. 2085-2092.

Donovan E., Bleakley N., Denholm E., et al., Randomised trial of standard 2D radiotherapy (RT) versus intensity modulated radiotherapy (IMRT) in patients prescribed breast radiotherapy, Radiotherapy Oncology, 2007, vol. 82, pp. 254-264.

Haffty B.G., Buchholz T.A., McCormick, B., Should intensity-modulated radiation therapy be the standard of care in the conservatively managed breast cancer patient?, Journal of Clinical Oncology, 2008, vol. 26, pp. 2072-2074.

Potters L., Steinberg M., Wallner P., et al., How one defines intensity-modulated radiation therapy, Int. J. Radiation Oncology Biol. Phys., 2003, vol. 56, pp. 609-610.

Chen G.P., Ahunbay E., Li, X.A., Automated computer optimization for 3D treatment planning of breast irradiation, Med. Phys., 2008, vol. 35, pp. 2253-2258.

Whelan T., MacKenzie R., Julian J., et al., Randomized trial of breast irradiation schedules after lumpectomy for women with lymph node-negative breast cancer, Journal of the National Cancer Institute, 2002, vol. 94, No. 15, pp. 1143-1150.

Shepard D.M., Earl M.A., Li, X.A., et al., Direct aperture optimization: a turnkey solution for step-andshoot IMRT, Med. Phys., 2002; vol. 29, pp. 1007-1018.

Van Asselen B., Schwarz M., Van Vliet-Vroegindeweij C., et al., Intensity-modulated radiotherapy of breast cancer using direct aperture optimization, Radiotherapy Oncology, 2006, vol. 79, pp. 162-169.

Beauchemin M., Thomson K.P.B., Edwards G., On the Hausdorff distance used for the evaluation of segmentation results, Canadian Journal of Remote Sensing, 1998, vol. 24, pp. 3-8.

Ahunbay E.E., Chen G.P., Thatcher S., et al., Direct aperture optimization-based intensity-modulated radiotherapy for whole breast irradiation, Int. J. Radiation Oncology Biol. Phys., 2007, vol. 67, pp. 1248-1258.

Zhang G., Jiang Z., Shepard D., et al., Direct aperture optimization of breast VRT and the dosimetric impact of respiration motion, Physics in Medicine and Biology, 2006, Vo. 51, pp. N357-N369.

McLnerney T., Terzopoulos D., Deformable models in medical image analysis: a survey, Medical Image Analysis. 1996. vol. 1 No. 2, pp. 91-108.

Pekar V., McNutt T.R., Kaus M.R., Automated model-based organ delineation for radiotherapy planning in prostatic region, Int. J. Radiation Oncology Biol. Phys., 2004, vol. 60, No. 3, pp. 973-980.

Carpmaels & Ransford, "Response to Extended European Search Report" for European Patent Application No. 11830160.5, dated Apr. 22, 2015, United Kingdom.

European Extended Search Report dated Sep. 25, 2014 in respect to EP application No. 11830160.5.

PCT International Search Report dated Jan. 19, 2012.

PCT Written Opinion dated Jan. 19, 2012.

PCT International Preliminary Report on Patentability dated Apr. 9, 2013.

Thomas G. Purdie et al., Automated Planning of Tangential Breast Intensity-Modulated Radiotherapy Using Heuristic Optimization, Int. J. Radiation Oncology Biol. Phys., vol. 81, No. 2, pp. 575-583, 2011, USA.

\* cited by examiner

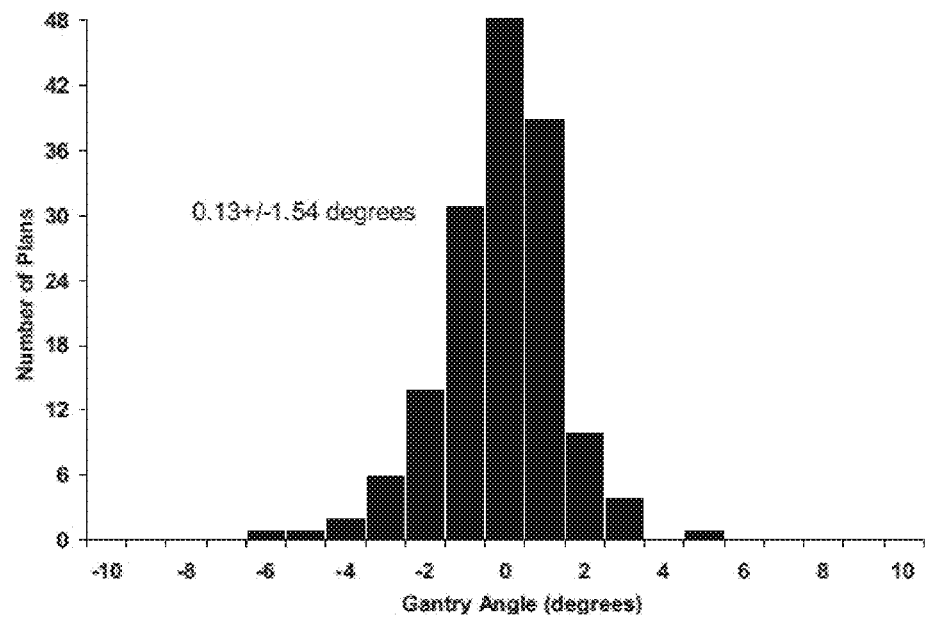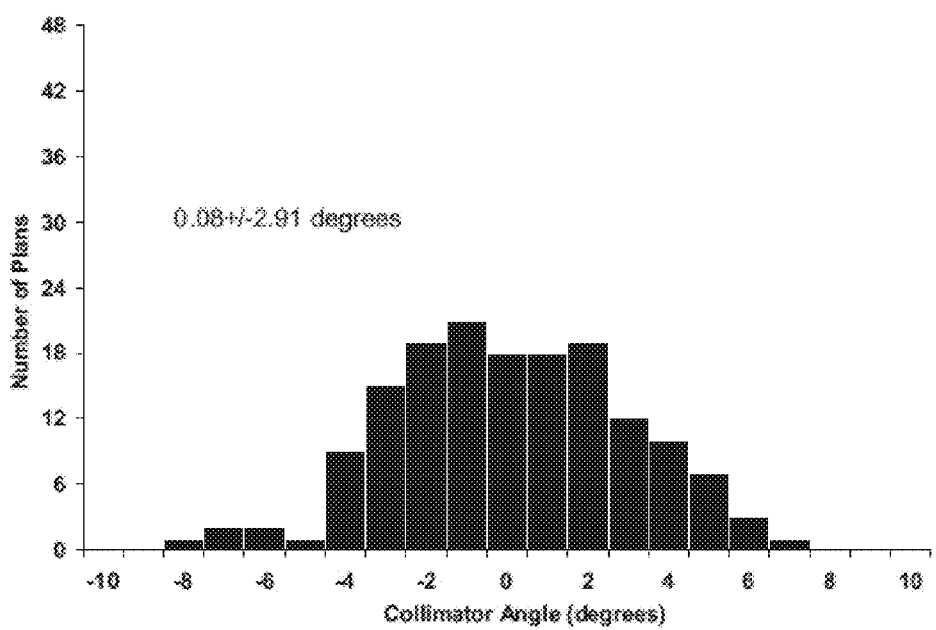
FIG. 2

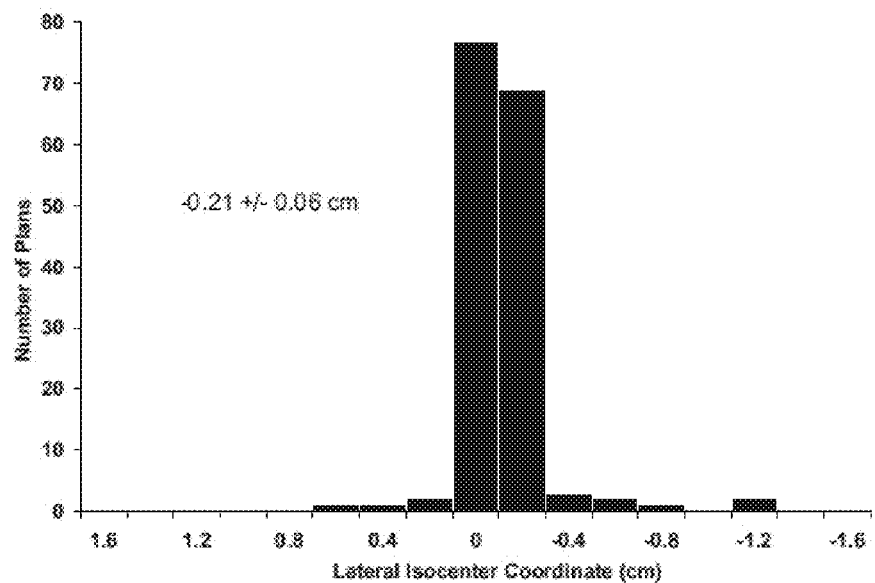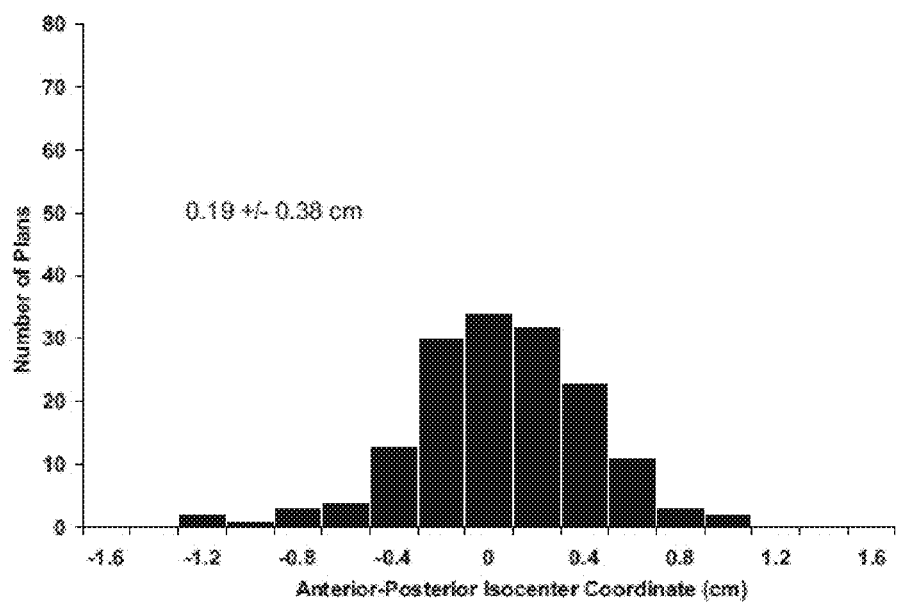
FIG. 4

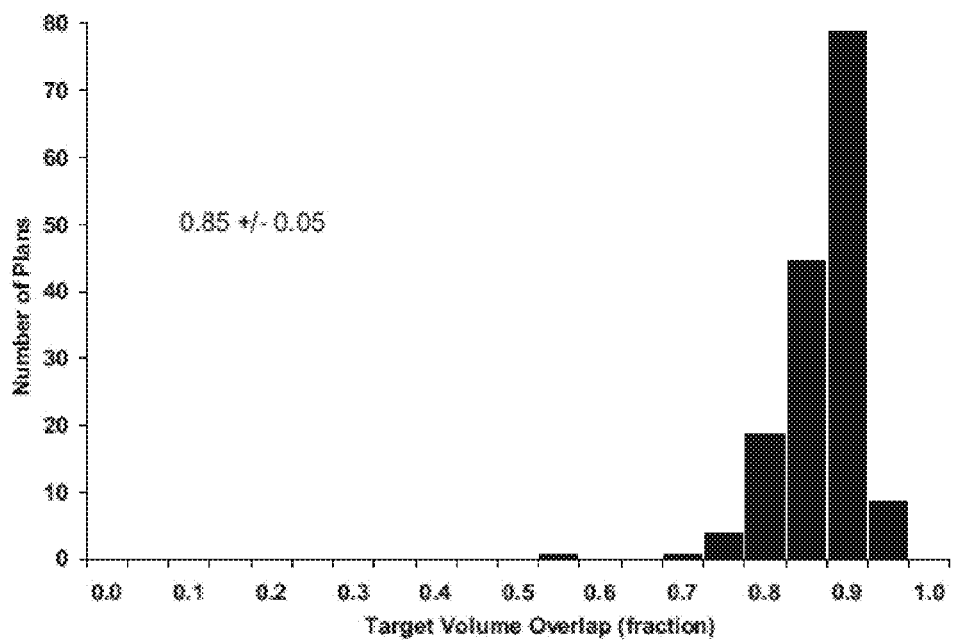
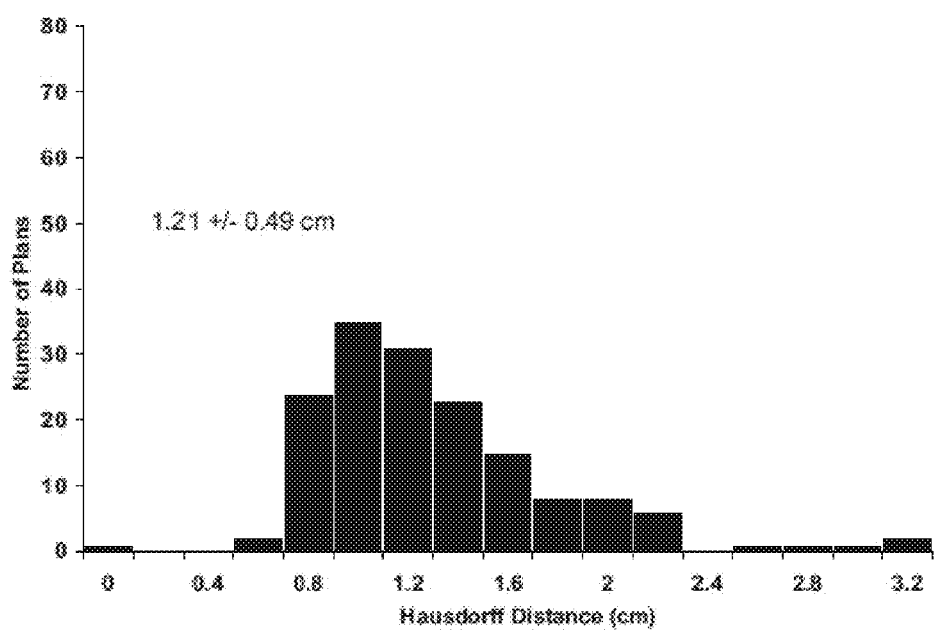
FIG. 5

| RMP Automated Tangential Breast IMRT | ☐ Advanced Settings |

SETUP
CT Simulator  V7.4 Generic: 120 kVp
Machine  SV02

TREATMENT
Prescription  4240 cGy in 16
Site  ◆ Whole Breast ◇ Chestwall   Mode ◆ Breast Coverage ◇ Lung Sparing

[ Start Automated Planning ]   [ Use Default Settings ]   [ Cancel ]

Fig. 9

```
------------------------------------------
General Summary (Flags:  1)
------------------------------------------
Mean Lung Area:        1.8 cm2 (2.0 cm2) .......... ok
Max Lung Distance:     2.4 cm  (2.0 cm ) >>>>>>> noted
CAVITY Margin:         1.1 cm  (1.0 cm ) .......... ok
Couch Removed Y:      -36.2 cm
------------------------------------------
Beam Summary (Flags:  0)
------------------------------------------
              MU   Limit              Weight  Limit
Medial
--- CP1 Open  140.0 (139.1) .......... ok  88.6% (75.0%) .......... ok
--- CP2        14.0  (20.0) .......... ok   8.9% (10.0%) .......... ok
--- CP3         4.0  (20.0) .......... ok   2.5% (10.0%) .......... ok
--- Total     158.0

Lateral
--- CP1 Open  144.0 (139.1) .......... ok  76.6% (75.0%) .......... ok
--- CP2         6.5  (20.0) .......... ok   3.5% (10.0%) .......... ok
--- CP3         7.6  (20.0) .......... ok   4.0% (10.0%) .......... ok
--- CP4        15.6  (20.0) .......... ok   8.3% (10.0%) .......... ok
--- CP5        14.3  (20.0) .......... ok   7.6% (10.0%) .......... ok
--- Total     188.0
------------------------------------------
Setup Summary
------------------------------------------
Lateral TTH from Chestboard:         7.0 cm
Set Depth at Medial Centre Tattoo:   6.3 cm
Then Shift:                          9.4 cm LEFT
Ant @ Isocentre Depth:               7.1 cm Medial  (Gantry=304°)(Coll=  6°)  Depth:  11.5 cm
Medial Field from Medial Tattoo:          --- cm  ON Lateral (Gantry=124°)(Coll=354°)  Depth:   8.0 cm
Lateral Field from Lateral Tattoo:         0.2 cm POST ------------------
Page 1 of 2
```

FIG. 12A

```
Dose Summary for 4240 in 16 fractions (Flags:  1)

Volume          Dose        Variation      Limit
aCTV (510.0 cc)
------ Max Dose         (2.0 cc)    4480 cGy (105.7%)   (<108%) ........... ok
------ Min Dose         (504.9 cc)  4030 cGy (95.0%)    (>92%)  ........... ok
------ Mean Dose                    4242 cGy (100.1%)   (97-103%) ......... ok aTreated Volume (1220.5 cc)
------ Max Dose         (2.0 cc)    4484 cGy (105.8%)   (<108%) ........... ok modCAVITY (9.9 cc)
------ Min Dose         (9.9 cc)    4076 cGy (96.1%)
------ Coverage         (9.8 cc)    4132 cGy (97.5%)    (>85%)  ........... ok DEVcavity (64.9 cc)
------ Min Dose         (64.9 cc)   3898 cGy (91.9%)
------ Coverage         (64.2 cc)   4106 cGy (96.8%)    (>95%)  ........... ok aLTLUNG (1038.5 cc)
------ Max Dose         (45.0 cc)   3870 cGy (91.3%)    (<50%)  >>>>>>> noted
------ Max Dose         (145.0 cc)  2043 cGy (48.2%)    (<50%)  ........... ok aHEART (550.5 cc)
------ Max Dose         (10.0 cc)   3556 cGy (83.9%)    (<90%)  ........... ok
------ Max Dose         (25.0 cc)   1894 cGy (44.7%)    (<50%)  ........... ok Page 2 of 2
```

FIG. 12B

Table 1. Example lookup table for IMRT optimization parameters.

|  | Target Volume | Automated Plans | Conventional Plans |
|---|---|---|---|
| Minimum Segment Area | < 200 | --- | 2 |
|  | < 300 | 2 | 4 |
|  | < 400 | 4 | 6 |
|  | < 500 | 6 | 8 |
|  | < 600 | 9 | 10 |
|  | < 800 | 12 | 12 |
|  | > 800 | 16 | 16 |
| Maximum Number of Segments | < 250 | 12 | --- |
|  | < 500 | 6 | 6 |
|  | < 1000 | 8 | 8 |
|  | < 1500 | 10 | 10 |
|  | > 1500 | 12 | 12 |

FIG. 13

Table 2. Example lookup table for gantry optimization distance lookup curves

| Algorithm Type | Coefficients | | Correlation |
|---|---|---|---|
| | Ln ($C_1$) | Linear ($C_2$) | ($R^2$) |
| Initial Mean Distance < 1.3 cm | | | |
|     Mean distance | 0.256 | 1.350 | 0.985 |
|     Mean distance (size correction) [1] | 1.000 | 1.300 | --- |
|     Maximum distance | 0.599 | 1.692 | 0.949 |
|     Maximum distance (size correction) [1] | 1.000 | 1.900 | --- |
| Initial Mean Distance > 1.5 cm | | | |
|     Mean distance | 1.022 | 0.866 | 0.981 |
|     Mean distance (size correction) [2] | 1.785 | 0.088 | 0.956 |
|     Maximum distance | 1.616 | 0.619 | 0.975 |
|     Maximum distance (size correction) [2] | 2.593 | -0.685 | 0.960 |

Example lookup equation:

Target distance for optimization = $(C_1)(Ln(Initial\ distance)) + C_2$

[1] Breast size correction applied to optimization when breast separation-height < 100 $cm^2$.

[1] Coefficients were not derived from a curve fitting, therefore no $R^2$.

[2] Breast size correction applied to optimization when breast separation-height > 200 $cm^2$.

FIG. 14

Table 3. Comparison of example treatment plan parameters.

| | Automated Plans | | | Conventional Plans | | | $p$ value |
|---|---|---|---|---|---|---|---|
| Monitor Units | | | | | | | |
| 200 cGy in 25 fractions | 267 | +/- | 11 | 269 | +/- | 11 | 0.26 |
| 265 cGy in 16 fractions | 355 | +/- | 15 | 353 | +/- | 15 | 0.54 |
| 250 cGy in 16 fractions | 334 | +/- | 13 | 332 | +/- | 10 | 0.34 |
| Number of Segments | 8.6 | +/- | 1.5 | 7.7 | +/- | 1.3 | < 0.001 |

Number of plans in each dose group: 200 cGy ($n = 26$), 265 cGy ($n = 100$) and 250 cGy ($n = 32$)
Statistical analysis according to paired $t$-test.

FIG. 15

Table 4. Example comparison of target volume dose-volume analysis

|  |  | Automated Plans | | | Conventional Plans | | | p value |
| --- | --- | --- | --- | --- | --- | --- | --- | --- |
| Minimum Target Dose | $D_{99\%}$ | 0.952 | +/- | 0.019 | 0.956 | +/- | 0.022 | 0.05 |
|  | $V_{95\%}$ | 0.981 | +/- | 0.081 | 0.982 | +/- | 0.082 | 0.67 |
|  | $V_{92\%}$ | 0.992 | +/- | 0.080 | 0.992 | +/- | 0.080 | 0.61 |
|  | $V_{90\%}$ | 0.993 | +/- | 0.080 | 0.933 | +/- | 0.079 | 0.52 |
| Maximum Target Dose | $D_{2cc}$ | 1.049 | +/- | 0.024 | 1.053 | +/- | 0.020 | < 0.001 |
|  | $V_{105\%}$ | 0.011 | +/- | 0.045 | 0.013 | +/- | 0.050 | 0.37 |

FIG. 16

Table 5. Example analysis of clinical acceptability of treatment plans

|  |  | Automated Plans | Conventional Plans |
|---|---|---|---|
| Clinically Equivalent |  | 125 79.1 % |  |
| Clinically Favorable | Maximum Plan Dose | 8 (4) | 3 (2) |
|  | Dose homogeneity within Whole Breast Volume | 5 | 16 |
|  | Minimum Dose to Whole Breast Volume | 0 | 1 |
|  | Minimum dose to Post-Surgical Cavity | 0 | 0 |
|  | Dose to Ipsilateral lung | 0 | 0 |
|  | Dose to Contralateral Breast | 0 | 0 |
|  | Dose to Heart | 0 | 0 |
| Total |  | 138 87.3 % | 145 91.8 % |
| Clinically Acceptable |  | 157 99.4 % | 156 98.7 % |

Parentheses indicate number of plans deemed significantly superior to alternate plan in side-by-side comparison.

Percentages are calculated from the 158 automated and manual plans reviewed.

FIG. 17

METHODS AND SYSTEMS FOR AUTOMATED PLANNING OF RADIATION THERAPY

CROSS-REFERENCE TO RELATED APPLICATION

The present application is a national stage entry of international patent application number PCT/CA2011/001130 filed on Oct. 6, 2011, which claims priority from U.S. provisional patent application No. 61/390,376, filed Oct. 6, 2010 and both of which are hereby incorporated by reference.

FIELD OF TECHNOLOGY

The present disclosure is related to methods and systems for radiation therapy planning. In particular, the present disclosure is related to methods and systems for automated planning of intensity modulated radiation therapy, such as for treatment of the breast.

BACKGROUND

Intensity modulated radiation therapy (IMRT) has been used for organ-preserving whole breast irradiation. IMRT also has been found to improve the ability to conform the treatment volume to concave tumor shapes, for example when the tumor is wrapped around a vulnerable structure such as the spinal cord or a major organ or blood vessel. In IMRT, computer-controlled accelerators distribute precise radiation doses to specified areas. The pattern of radiation delivery is determined using tailored computing applications to perform optimization and treatment simulation (commonly referred to as treatment planning). The radiation dose applied to the patient is controlled by controlling, or modulating, the radiation beam's intensity. In a typical treatment plan, the radiation dose intensity is elevated near the gross tumor volume while radiation among the neighboring normal tissue is decreased or avoided completely, in order to maximize dose to the target tissue (typically the tumor) while minimizing dose to non-target tissues.

In some examples, IMRT has been shown to improve target dose homogeneity (1, 2) and reduce acute skin toxicity (3, 4) over conventional breast radiation therapy approaches that rely on wedged compensators for beam modulation. In some examples, the dose distributions produced with IMRT have also translated into better clinical results versus conventional methods, as shown in two randomized trials (4, 5). The use of IMRT in breast radiation therapy and how one defines IMRT in the context of breast treatment has been debated (6, 7). As well, greater amounts of resources and expertise are often required to implement and maintain a breast IMRT planning approach (7).

An example of automated planning for breast tangents has previously been implemented for three-dimensional conformal breast tangents treatment plans (8). That algorithm was developed to optimize beam energy, beam weighting, wedge angle and wedge orientation, to produce treatment plans. In that example, the automated process was found to reduce the planning time and to result in more reproducible plans as compared to the conventional clinical manually-designed plans. However, that example was not related to IMRT. Further, in that example, not all of the planning was automated, for example determination of parameters such as gantry angle and collimator angle was not automated, nor regions of interest segmentation nor incorporation of the cavity into the optimization.

Automation for IMRT may involve optimization parameters, such as the number of segments and minimum area of segments allowed for generating the modulated field, that do not need to be considered in conformal treatment plans. Such IMRT parameters should be considered to help ensure that generated treatment plans are able to provide sufficient modulation without making the segments too complicated, for example.

It would be desirable to provide a method and system for treatment planning of radiation therapy that avoids or reduces the need for extensive user interaction and iterative trial-and-error to generate treatment plans

SUMMARY

The present disclosure, in some aspects, provides for automation of a portion or all of the treatment planning process for IMRT, in particular whole-breast IMRT. In the disclosed methods and systems, IMRT may be performed using fewer resources and comparable throughput times as conventional radiation treatments by automating steps in the planning process. This automation may be based on empirical and/or historical data and/or relationships. The disclosed automated treatment planning process may require relatively little user interaction and/or trial-and-error. Common anatomical landmarks, such as those identified in computer tomography (CT) simulation and a relatively small number of clinical options can facilitate the entire automated treatment planning process.

The present disclosure describes the automation of treatment planning for tangential breast IMRT. In particular, the present disclosure provides examples of automated techniques for two-field tangential breast IMRT planning. However, it should be understood that the disclosed methods and systems may be useful for treatment planning for other treatment sites. In addition, the disclosed methods and systems may be extended to other treatment techniques. For example, in breast radiation therapy, the disclosed methods and systems may be used in partial breast radiation therapy and supraclavicular and axilla regions, in addition to whole breast and chest wall therapy.

The present disclosure, in some aspects, also provides a user interface for automated generation of a IMRT treatment plan, for example for breast treatment planning.

In some aspects, there is provided a method for automated planning of radiation therapy treatment, the method including, at a processor: determining at least one region of interest for the radiation therapy treatment; determining at least one clinical requirement to be met for the radiation therapy treatment, the at least one clinical requirement being applied to the at least one region of interest; calculating at least one technical parameter to satisfy the at least one clinical requirement using at least one optimization parameter determined from a predefined empirical relationship; and generating a treatment plan comprising a set of technical parameters, including the at least one calculated technical parameter, for the radiation therapy treatment.

Determining the optimization parameter may include obtaining an empirical value from a lookup table. The lookup table may contain empirical values determined from a plurality of previously used treatment plans.

The optimization parameter may be one of: a segment number, a segment area, a maximum lung distance value, and an average lung distance value.

The at least one region of interest may be determined using an imaging modality selected from: magnetic resonance (MR), computer tomography (CT), cone-beam CT (CBCT), and positron emission tomography (PET).

The at least one technical treatment parameter may include at least one of: a gantry angle, a collimator angle, a collimator jaw setting, a treatment beam isocenter, and a treatment beam strength.

The method may further include displaying a user interface for inputting the user-specified clinical requirement. The user interface may provide at least one predefined default setting.

The radiation therapy may be for treatment of breast tissue.

The at least one clinical requirement may include at least one of specification of allowable non-target tissue in treatment field; specification of margin of coverage of target tissue; prioritization of coverage of target tissue; prioritization of avoidance of non-target tissue; and restriction of adjustments for one or more technical parameters.

In some aspects, the present disclosure provides a non-transitory computer program product tangibly embodying code that, when executed by a processor, causes the processor to carry out the methods described above.

In some aspects, the present disclosure provides a system for automated planning of radiation therapy treatment, the system including at least one processor coupled to at least one memory having computer-readable instructions encoded thereon, wherein the processor is configured to execute the instructions to carry out the methods described above.

The system may further include a display coupled to the processor for displaying a user interface, and an input device coupled to the processor for inputting the user-specified clinical requirement using the user interface.

BRIEF DESCRIPTION OF THE DRAWINGS

Example embodiments of the present disclosure will be described with reference to the drawings, in which:

FIGS. 2-4 show charts illustrating an example distribution of differences between automated and conventional plans for example IMRT parameters;

FIG. 5 shows charts illustrating distribution of volume overlap and Hausdorff distances between treatment volumes calculated using an example automated method compared to conventional methods;

FIG. 9 shows an example user interface suitable for an example method of automated radiation therapy treatment planning;

FIGS. 12A-12B shows examples of a report provided after a treatment plan has been automatically calculated;

FIGS. 13 and 14 illustrate example lookup tables that may be used for calculations in an example method of automated radiation therapy treatment planning;

FIGS. 15 to 17 illustrate comparisons of an example study for an example method of automated radiation therapy treatment planning to conventional methods.

DETAILED DESCRIPTION

Overview

Figure 1:
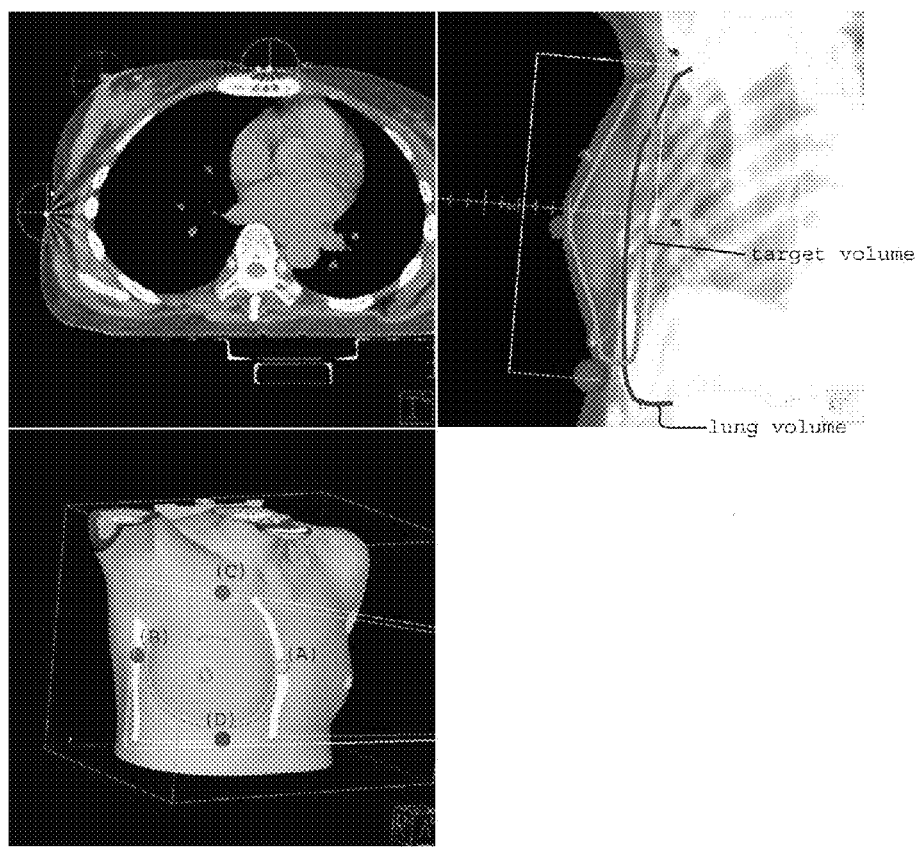
FIG. 1 illustrates example CT images of a treatment area.

In some aspects, the present disclosure provides methods and systems for automated planning for radiation therapy treatment, for example of breast tissue.

Methods for automated planning for radiation therapy treatment may be carried out using, for example, conventional treatment planning systems or workstations, including a processor that executes computer-readable instructions (e.g., stored in a memory coupled to the processor) in order to carry out these methods.

In some examples, the methods and systems may include the use of two or more processors, such as where a portion of the steps are carried out by one processor (e.g., an imaging workstation may be used for automated image delineation) and another portion are carried out by another processor (e.g., a treatment planning system may be used for automatically calculating treatment parameters). In such cases, the two or more processors may communicate with each other (e.g., via a wired or wireless connection, such as an intranet) or the appropriate data may be transferred between processors manually by a user.

In this disclosure, processor or processors suitable for carrying out methods for automated treatment planning may be referred to generally as a system for automated treatment planning.

The example methods and systems described herein may determine a value of at least one technical parameter for a treatment plan based on at least one clinical requirement input by a user. The technical parameter(s) may be automatically calculated using optimization algorithms and/or automatically selected based on one or more empirical rules/relationships. The optimization algorithms used may be the same or similar to those used in conventional treatment planning methods. Such optimization algorithms may require selection of one or more optimization parameters.

Predefined empirical data and/or relationship(s) may be used to automatically determine the optimization parameter(s) and/or technical parameter(s) based on the clinical requirement(s). A treatment plan for radiation therapy may be automatically generated based on the determined technical parameter(s).

DEFINITIONS

The term "clinical requirement" may be used to refer to any treatment-specific or outcome-specific requirement that may be specified by a user (e.g., a clinician or oncologist). Typical clinical requirements for radiotherapy planning may include, for example: amount of non-target tissue that may be irradiated, minimum amount of coverage of the target area, and prioritization of which areas to irradiate/avoid. Examples specific to treatment of the breast are discussed in greater detail below. A single clinical requirement may require multiple technical parameters in order to be satisfied. Thus, change in a single clinical requirement may require adjusting multiple technical parameters. Clinical requirements are often inter-related, overlapping or even contradictory, and may require proper prioritization and complex calculations of the technical requirements in order to achieve a clinically acceptable treatment plan.

The term "technical parameter" may be used to refer to any parameter that controls the technical operation of the treatment system. Typical technical parameters may include, for example: gantry angle, collimator angle, beam isocenter position, collimator jaw setting and beam strength. Examples are discussed in greater detail below. A single technical parameter may affect multiple clinical outcomes. Thus, change in a single technical parameter may affect whether multiple clinical requirements are satisfied. The relationship between each technical parameter and each clinical outcome (and the degree to which each clinical requirement is satisfied) may not be intuitive or easily understood. In conventional treatment planning, technical parameters may be manually selected based on the personal experience, intuition and knowledge of the clinician or radiation therapy treatment planner (dosimetrist), usually involving a trial-and-error approach, and thus may not be reproducible, reliable or easy to determine. In the presently disclosed systems and methods, a technical parameter may be automatically determined based on one or more empirical rules/relationships, or may be automatically calculated using an optimization parameter.

The term "optimization algorithm" may be used to refer to an algorithm for calculating an optimum (e.g., maximum or minimum) value, typically subject to one or more constraints. It should be understood that although the term "optimization" is used throughout this disclosure, the result of optimization may not always be strictly optimal; for example, the result may be less than optimal due to error, uncertainly or safety factors. Commonly used optimization algorithm may involve iterative calculations in which a treatment field is calculated for a candidate treatment plan or a candidate technical parameter value, and evaluated based on the specified clinical requirements. If the candidate treatment plan or candidate technical parameter value fails to satisfy the clinical requirements, the technical parameter is adjusted and retested iteratively.

The term "optimization parameter" may be used to refer to a value, typically an empirical value, that may be used in the optimization algorithm (e.g., as a weight, bias, coefficient or constant) to direct, train, constrain or limit the optimization algorithm. Selection of the appropriate type of optimization parameter and the appropriate value for the optimization parameter is often crucial for effective optimization, but may not be intuitive or easily learned. Selection of the optimization parameter(s) for optimization of the technical parameter(s), in order to achieve the clinical requirement(s), in conventional treatment planning, may be highly dependent on the personal experience, intuition and knowledge of the clinician or radiation therapy treatment planner (dosimetrist), and may be ultimately based on trial-and-error. In the presently disclosed systems and methods, an optimization parameter may be automatically determined based on empirical rules/relationships.

The term "empirical rule/relationship" may be used to refer to methods and data, such as lookup tables and lookup curves, that provide values empirically determined from previously used treatment plans. Other methods, such as the use of statistical models or machine learning, may be used to implement such empirical rules/relationships. Such empirical values may be technical parameters and/or optimization parameters that have been found to achieve the desired clinical requirements. An empirical rule/relationship may be dependent on specific treatment and/or patient conditions. In the presently disclosed methods and systems, the appropriate empirical rule/relationship may be automatically used to determine a suitable technical parameter or optimization parameter. For example, in the case of treatment of the breast, different empirical coefficients may be automatically selected for a lookup curve to accommodate different breast sizes.

Examples of Clinical Requirements

The following examples make reference to treatment of breast tissue. For treatment planning in treatment of breast tissue, typically markers are used to identify the region of interest and to be used during treatment, to help ensure that the patient's position is the same as the position on which the treatment plan is based. Thus, such markers may be used for identifying the target volume for treatment planning as well as used for setting up the patient at treatment.

Such markers may be identified during CT simulation and may be used to delineate structures of interest, such as the target tissue, the post-surgical cavity (seroma) in the target tissue and non-target tissues. FIG. 1 shows an example of markers and delineated structures commonly used in treatment planning for treatment of breast tissue. The bottom image shows an example surface rendering of a patient, showing the medial (A), lateral (B), superior (C) and inferior (D) markers, as well as a wire marker outlining the breast. These markers are used to delineate the target tissues and non-target (e.g., lung tissues), for example as shown in the upper right image of FIG. 1.

A clinical requirement may be defined as any physiological or clinical requirement for the treatment plan. Example clinical requirements include, for example: a maximum amount of normal tissue that may be irradiated, a minimum amount of target tissue that must be irradiated, a maximum amount of irradiation for a patient, and certain tissues that should be excluded or included in the irradiation.

Examples of clinical requirements that may be considered, particularly for treatment of breast tissue, include:

A) Medial and lateral beam placement: the user is able to fix the placement of the treatment beam on the medial and lateral aspects of the patient. The user may choose to have the beam fall on one or both of the medial and lateral markers. This clinical requirement may be clinically important to provide gross control over how much breast tissue is irradiated. When the user wants to ensure at least part of the breast is covered (i.e., ensure that the beam is not placed inside the medial marker), the user may fix the beam to the medial marker. As well, if the user wants to ensure that extra tissue is not irradiated beyond the lateral marker, the user may fix the beam to the lateral marker. Although this clinical requirement has been described with respect to treatment of breast tissue, it should be understood that, in other applications, a similar clinical requirement may be used to fix the placement of beams to other markers on the patient.

B) Lateral beam placement: the user is able to specify the placement of the treatment beam through the lateral part of the patient. The user may choose to force the beam to move anteriorly or posteriorly, or to allow automated calculations to determine the appropriate direction, based on other clinical requirements. This may be clinically significant to control the amount of breast tissue treated. When the user wants to limit the amount of breast treated, the user may require the lateral part of the beam to be placed only anterior of the breast marker and thus spare more breast tissue. If the user wants to be generous with coverage and possibly cover more breast tissue than normal, the user may require the lateral part of the beam to only be placed posterior of the breast marker. Although this clinical requirement has been described with respect to treatment of breast tissue, it should be understood that, in other applications, a similar clinical requirement may be used to specify directional placement of the treatment beam in other tissues.

C) Lung volume: the user is able to specify an allowance for more or less (or none) of the lung to be irradiated by the treatment beam. The amount of the lung in the treatment field is commonly referred to as "lung volume" for brevity. By allowing more of the lung to be irradiated, the user may ensure that the entire breast volume is covered. In contrast, by allowing less (or none) of the lung to be irradiated, the user may ensure that the lung dose is minimized (e.g., for patients who have had previous treatments, small lungs or poor lung function). The allowed lung volume may be specified qualitatively or quantitatively. Quantitative specification of lung volume may be based on distance in cm, in which the average distance for each point defining the three dimensional lung volume is calculated. For example, if a user has a hard numerical constraint they wish to achieve then this number may be directly specified. Alternatively, the user may use a qualitative specification, such as "less lung" or "more lung". The disclose methods and systems may have predefined values for "less lung" and "more lung". Typically, treatment plans allow for 1.0-2.0 cm of lung in the field, and 1.5 cm may be considered average. However, if a user wanted to irradiate essentially no lung volume, this clinical requirement may be specified to a lung volume of 0.5 cm, for example. Although this clinical requirement has been described with respect to treatment of breast tissue, it should be understood that, in other applications, a similar clinical requirement may be used to specify the allowance of other non-target tissues that may be in the treatment field.

D) Maximum lung distance: similar to the lung volume specification described above, but specifies the maximum lung volume that may be treated.

E) Breast size correction: the user is able to specify whether the breast size of the patient should be a consideration in generating the treatment plan, with the breast size of the patient specified, typically in terms of breast separation and height. This allows the treatment plan to be automatically calculated while taking into account the size of the patient's breast. For example, the user may specify the breast size correction to be applied in order to irradiate less lung volume for patients who have small breasts (typically for patients who may be smaller in general). Although this clinical requirement has been described with respect to treatment of breast tissue, it should be understood that, in other applications, a similar clinical requirement may be used to take into account the patient size, patient shape, or the size and/or shape of the target to be treated.

F) Cavity optimization: the user is able to specify a margin from the outer edge of the treatment field and the edge of the delineated post-surgical cavity. Specification of a positive value for the margin may help to ensure that the entire post-surgical cavity is included in the treatment field and avoid underdosing the cavity target at the edges of the treatment field. A negative value specified for this requirement may indicate that the beam is to fall within the target volume by the specified value. This clinical requirement may be applicable to treatment of any delineated tumor or other targets of interest. As will be explained below, cavity optimization may be performed in conjunction with wire optimization, and this clinical requirement may be applied after gantry optimization has been calculated according to the requirements described above.

G) Medial proximity correction: the user is able to specify a correction to provide as much medial coverage as possible for tumor cavities that are located medially. Although this clinical requirement has been described with respect to treatment of breast tissue, it should be understood that, in other applications, a similar clinical requirement may be used to include correction factors for the location of tumors in other anatomical positions.

H) Wire inside/outside the beam: the user is able to specify that the marker wire defined in the reference axial plane is within or outside of the treatment field. In treatment of breast tissue, a wire may be used to outline the breast at the time of CT simulation, for example. If the user does not wish to compromise treatment of the entire breast, the user may choose to ensure that treatment beam covers an area that is equal to or larger than that outlined by the wire. On the other hand, if the user wishes to limit the dose to lung, heart and/or total breast volume at the cost of not treating breast tissue as defined by the wire, the user may choose to ensure that the beam covers an area that is less than that outlined by the wire, for example. This may be specified for one or both of the medial and lateral side of the beam, independently. For example, in a patient who has had previous treatment to the contra-lateral breast, the user may wish to provide an extra margin of untreated tissue in the medial direction at the expense of covering the breast tissue, but avoid compromised coverage of the breast laterally. Thus, the user may choose to have a margin of 4.0 cm for the medial part of the beam and a margin of 0.0 cm for the lateral part of the beam, for example. Although this clinical requirement has been described with respect to treatment of breast tissue, it should be understood that, in other applications, a similar clinical requirement may be used to specify the treatment field with reference to other markers.

I) Wire coverage overrides shielding avoidance: the user is able to prioritize coverage of the wire over any specified shielding of non-target tissues. This may be specified when the user wishes to treat the entire wire area, regardless of whether shielded tissues overlap the wire area. Although this clinical requirement has been described with respect to treatment of breast tissue, it should be understood that, in other applications, a similar clinical requirement may be used to prioritize treatment of target tissues over avoidance of non-target tissues. Similarly, another clinical requirement may be to prioritize avoidance of non-target tissues over treatment of target tissues.

J) Wire coverage overrides gantry: the user is able to prioritize coverage of the entire wire over gantry optimization. This may be specified when the user wishes to treat the entire wire area, even if other specified gantry requirements (e.g., in A) above) are in conflict. Although this clinical requirement has been described with respect to treatment of breast tissue, it should be understood that, in other applications, a similar clinical requirement may be used to prioritize treatment of target tissues over optimization specifications. Similarly, another clinical requirement may be to prioritize avoidance of non-target tissues over optimization specifications.

K) Shielding: the user is able to define how non-target tissues, such as the heart, tissue inferior of the diaphragm and the humerus, are shielded from treatment. The user may specify how large a margin of avoidance should be used for non-target tissues. For example, if a patient has had previous treatment, more shielding may be desirable to ensure that non-target tissues are not treated. Typically, shielding is defined by the amount of non-target tissue allowed in the field. The remaining tissue is shielded. For example, the user may specify that up to 1.0 cm of the heart is allowed to be in the treatment field, or if the patient has had previous heart complications, the user may specify a value of 0.0 cm so that no heart tissue may be in the treatment field. This clinical requirement may be general to all non-target tissues, or may be specified for individual non-target tissues. Although this clinical requirement has been described with respect to treatment of breast tissue, it should be understood that, in other applications, a similar clinical requirement may be used to specify shielding for other non-target tissues.

Examples of Technical Parameters

A technical parameter may be defined as any technical setting for the treatment system and treatment beams. Example technical parameters include, for example: location of beam isocenter, value of gantry angle for each treatment beam, value of collimator angle for each treatment beam, and the dose delivered (strength) from each treatment beam, among others.

Examples of technical parameters that may be used to control the treatment system and beams, particularly for treatment of breast tissue, include those listed below. Although described with respect to treatment of breast tissue, it should be understood that the same or similar technical parameters may be applicable to IMRT treatment of other target tissues (e.g., prostate or head and neck).

1) Gantry angle: this parameter is typically adjusted to achieve one or more desired clinical requirements. These clinical requirements may be prioritized such that the gantry angle is optimized to accommodate a higher priority clinical requirement over a lower priority clinical requirement. In the case of treatment of breast tissue, these clinical requirements may include on or more of, in order of lowest to highest priority: a target lung volume (e.g., determined from an empirical lookup table); wire and marker constraints for the whole breast volume (this may also affect the target lung volume); a desired cavity optimization; and a desired wire optimization. For optimization of post-surgical cavity coverage (e.g., to satisfy a specified cavity margin), the distance from the outer edge of the calculated treatment beam to the edge of the delineated post-surgical cavity may be calculated and once a gantry angle satisfies the set cavity coverage, the gantry angle may be finalized. For wire optimization, the wire may be delineated from the image data and used to adjust the gantry angle to achieve the specified wire coverage.

3) Beam isocenter: this parameter specifies the position of the isocenter of the beam and thus defines the centre of the treatment field. The beam isocenter should be positioned to match the centre of the desired target tissue or treatment area for most treatment sites. More typically in tangential breast geometries, for example, the isocenter may be positioned at the posterior edge of the field with only half the field opened and the other half of the field blocked. In some applications, such as for treatment of breast tissue, this parameter may be controlled by controlling the gantry angle, such that any clinical requirement that affects the gantry angle may also affect the beam isocenter. In other applications, this parameter may be independently controlled.

4) Collimator angle: the collimator angle specifies the angle in which the beam is rotated along its central axis. Rotation of the beam may be carried out to reduce shielding and reduce beam divergence into non-target tissues. For example, in the case of treatment of breast tissue, the beam may be rotated such that it is oriented essentially parallel to the lung, to reduce beam divergence into lung tissue. This parameter may be optimized to achieve the desired treatment area, for example taking into account any desired shielding of non-target tissues. The beam achieved based on this parameter may be considered the primary beam segment for IMRT treatment. Additional beam segments may be created and added to this primary segment to achieve a final treatment plan. In addition to the collimator angle, the gantry angle and beam isocenter play a role in controlling the beam shape and size, and the final treatment field. The collimator angle may be re-optimized each time the gantry angle and/or beam isocenter values are changed.

5) Beam energy: this specifies the irradiation intensity of the treatment beam, and may directly impact the dosage applied to the treated tissues.

Relationship Between Clinical Requirements and Technical Parameters

Typically, the value of the technical parameter(s) needed to achieve the specified clinical requirement(s) may not be easily determined manually. For example, in many cases, changing a single technical parameter may affect several different clinical outcomes and similarly achieving a single clinical requirement may need adjustment of several different technical parameters. For example, specification of a single clinical requirement may require the adjustment of the gantry angle, beam isocenter, collimator angle and beam size, as well as to beam energy, among others. In addition, specification of a clinical requirement may require adjusting IMRT parameters such as the number of segments, the minimum segment area of the segments, the dose contribution of the segments and dose-volume objectives for IMRT optimization, among others.

Consider, for example, a clinical requirement to fix the medial part of the beam to treat more breast tissue, with a specified margin. This requirement is intended to fix the medial part of the beam to pass through the medial marker and only allow for adjustment of the lateral part of the beam. To achieve this clinical requirement, the automated calculations may constrain the beam isocenter placement such that the beam is variable only on the lateral side (e.g., if the calculated treatment beam is found to be too shallow on the patient, then the gantry angle needs to be steeper and the isocenter is adjusted down). The cavity and/or wire margin specified is then considered. The gantry angle, beam isocenter and collimator angle are adjusted until the treatment margin is at least equal to that specified. In this simple example, multiple technical parameters are adjusted to fit a single clinical requirement. The clinical requirement may also constrain the range and/or type of technical parameters that may be adjusted.

A treatment plan typically has multiple clinical requirements, which affect overlapping technical parameters. For example, in addition to the fixed medial beam specified in the above example, the clinician may additionally desire a clinical requirement to allow the wire to be outside the treatment area (e.g., to avoid treating tissues outside the breast). This additional boundary condition sets the range in which the gantry angle may be adjusted on both the medial and lateral side based on the wire position. Thus, the fixed medial beam requirement limits the parts of the gantry that may be adjusted, while the wire coverage specification may limit the range in which the gantry angle may be adjusted.

In some instances, clinical requirements may require conflicting technical parameters to achieve, in which case a compromise may be necessary. These numerous and complex relationships, which may be conventionally not well understood and only achieved by trial-and-error, may all be automated in the disclosed methods and systems.

Although optimization algorithms may be used to optimize a technical parameter according to the clinical requirement(s), such optimization is often dependent on appropriate selection of the optimization parameter(s). Optimization may be highly sensitive to the selection of the optimization parameter(s), and the selection of the optimization parameter(s) may have a complex dependency on the clinical requirement(s). In conventional treatment planning, selection of the optimization parameter(s) is typically highly subjective and is based on the intuition, training and experience of the clinician and the radiation therapy treatment planner (dosimetrist).

Methods and Systems for Automated Treatment Planning

The methods and systems for automated treatment planning may be designed to automate some or all of the volume delineation, beam placement and IMRT treatment planning steps conventionally carried out manually by the treatment planning radiation therapist. For example, in breast treatment planning, the automated treatment planning methods and systems may use the radio-opaque markers placed during CT simulation as inputs and may calculate (e.g., optimize) the tangential beam parameters to geometrically reduce or minimize the amount of lung and heart treated while covering most or all of the whole breast volume. These and other IMRT parameters may be calculated based on the automatically delineated target volume (e.g., whole breast volume).

Figure 8:
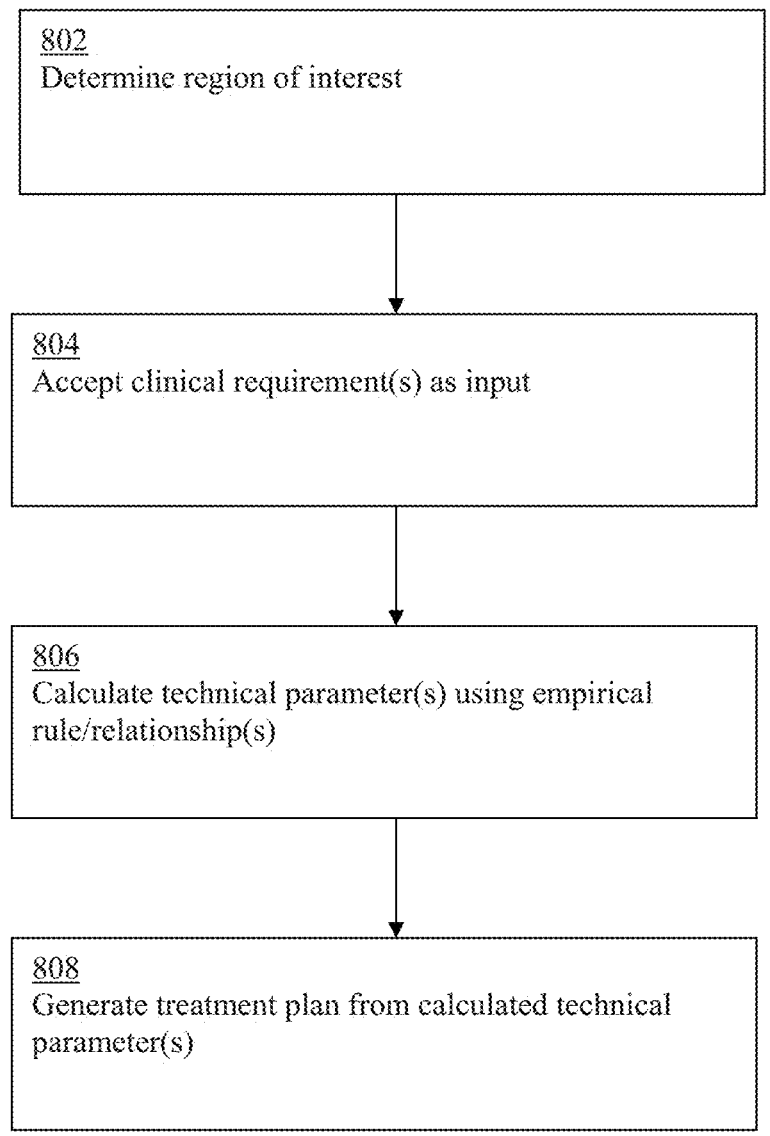
FIG. 8 is a flowchart illustrating an example method of automated radiation therapy treatment planning.

Reference is now made to FIG. 8, which is a flowchart illustrating a method for automated planning of radiation therapy.

At 802, one or more regions of interest may be determined. This may include identifying markers on a pre-obtained image (e.g., using magnetic resonance imaging (MRI), positron emission topography (PET), CT or cone-beam CT (CBCT)) of the target tissue, including any anatomical markers. Suitable markers may include inherent anatomical features (e.g., a bone feature or a cavity feature) and/or introduced markers (e.g., radio-opaque markers, fluorescent markers). Such markers (whether inherent or introduced) may be the same as or based on clinically accepted markers for conventional treatment planning, such as described in (1).

Different types and/or configurations of markers may be used for different treatment targets and/or different imaging modalities. A marker may be placed externally (e.g., on the skin of the patient) or internally (e.g., a clip or other surgical marker). In some examples, no markers may be necessary, for example where anatomical features are used in place or markers or other image processing software is used to define the treatment area.

In examples where the image is a CT image, conventional radio-opaque markers may be used. For example, for treatment of breast tissue, the radio-opaque markers may include: i) a superior marker; an inferior marker; iii) a medial marker; and iv) a lateral marker, for example as shown in FIG. 1. Where the entire actual breast is not delineated, a radio-opaque wire (e.g., as imaged in a CT scan) outlining the breast tissue may be used to define the breast volume. This wire may be referred to as a wire marker and the outlined area may be referred to as a wire area.

Identification of the markers and the region(s) of interest may be carried out automatically, for example using a conventional delineation or marker identification algorithm. Identification of the markers and delineation may also be done separately and this information provided to the system. Thus, determining the region of interest may include simply receiving data identifying the region of interest.

The markers may be automatically located by the automated treatment planning system using suitable marker-locating algorithms. For the example markers described above for treatment of breast tissue, the markers corresponding to the medial, lateral, superior and inferior extent of the breast may be automatically identified and a point of interest may be defined for each marker. In addition to these introduced markers, the system may also automatically determine inherent anatomical markers using suitable algorithms, such as identification of the apex of the breast on the isocenter image slice to define an anterior point.

In some examples, the markers may be determined based on an automatic delineation of the target tissue. For example, delineation of the entire breast may be automatically carried out using conventional methods (e.g., at an imaging workstation), such as described in (1), and appropriate markers may be located and identified based on this 3D volume (e.g., similar to the markers described above).

The target tissue region may be identified using other methods including a defined target point or points, target plane, target volume, target outline, or a combination thereof, among other methods.

Any method of identifying the target tissue and other regions of interest may be suitable. In some examples, where physical markers are not used, the location of the markers may be extrapolated or calculated after delineating the target tissue, such that virtual marker locations may be used for other calculations. For example, where the entire breast region is defined without the use of physical markers, the virtual locations of medial, lateral, superior and inferior markers (e.g., as described above) may be calculated automatically for use in optimization calculations, such as those described below.

In some examples where the marker location is not needed for any calculations, it may not be necessary to supply or calculate marker locations. For example, the whole breast volume may be segmented and analogous points to conventional markers may be identified. Alternatively, optimization calculations may not rely on marker points and instead rely on the entire actual breast volume.

Determining the region of interest (ROI) may include automatic delineation by the system. For example, in the case of breast treatment, ROIs may include non-target tissue such as the lungs, heart, ribs, diaphragm and tissues inferior to the diaphragm (e.g., liver, spleen and stomach) as well as any wire marker placed on the patient. The wire marker may be used to represent the breast volume. In some examples, where the entire actual breast is delineated, delineation of the wire may not be included. These example ROIs may be automatically delineated in addition to all other tissue that may normally be assessed by a user (e.g., a planner or clinician) during normal planning.

This automatic delineation may be carried out by the treatment planning system, for example using model-based segmentation (MBS) adaptation and/or image thresholding methods. These methods may be included as components of a conventional treatment planning system. Any other suitable method for automatic delineation of ROIs may also be used (e.g., using different markers, target points, ROIs, thresholds, etc.), such as described in (15).

Adaptation using MBS may generate organs as three-dimensional polygonal surface meshes defined by a collection of vertices. Following adaptation, these meshes may be then converted to Cartesian co-ordinates to define ROI volumes, such as described in (16).

The identified anatomical markers and delineated ROIs may be transmitted as input for automatically calculating appropriate treatment planning parameters and automatically generating a treatment plan. For example, 802 may be performed by a conventional imaging workstation and the identified markers and ROIs data may be transferred (automatically or manually) to a treatment planning workstation for subsequent steps.

At 804 one or more clinical requirements are determined. The clinical requirement(s) may be set by a user. For example, the user may be provided with options (e.g., through a user interface, described in greater detail below), to set clinical parameters for the treatment plan, including any threshold limits. The user may be restricted in the range of values selectable as a threshold. For example, the user may be presented with user interface including a slider for selecting a threshold value from a predefined range of values.

For example, for planning treatment of breast tissue, selection of thresholds may be restricted to a predefined range of values as described below:

The amount of mean lung distance (cm) allowed in the treatment field may be selectable in the range of 0.0-4.0 cm.

The amount of maximum lung distance (cm) allowed in the treatment field may be selectable in the range of 0.0-4.0 cm. This threshold may compete with the mean lung distance threshold and only one of these two thresholds may be in use for a given treatment plan.

The desired cavity margin may be selectable in the range of −2.0 to 2.0 cm. A negative value for this threshold may indicate that the treatment field may intersect the cavity by that value, while a positive value may indicate that the distance between the cavity and the outmost perimeter of the treatment field must be at least this value.

The margin of wire coverage by the beam may be selectable in the range of 0.0-4.0 cm. This translates into a boundary condition for gantry optimization. A value of 0.0 may indicate that the beam extends to match the wire, while a value of 4.0 may indicate that the beam coverage may lie inside the wire to a maximum of 4.0 cm.

The amount of wire shielding may be selectable in the range of 0.0-4.0 cm. This defines the minimum distance between any shielding and the wire.

The gantry optimization wire margin may be selectable in the range of −2.0-2.0 cm. A positive value may indicate that the beam may be placed outside the wire with a margin greater than or equal to the specified value, while a negative value may indicate that the beam may be placed inside the wire up to the specified value. This restriction may be used to specify the desired margin to achieve during wire optimization.

The shielding organ margin may be selectable in the range of 0.0-4.0 cm. This defines the margin for allowing non-target organs in the treatment field. For example, if 1.0 cm is selected, this may indicate that up to 1.0 cm of a non-target organ, such as the heart, is allowed to be within the treatment field.

The high energy threshold (also referred to as separation threshold) may be selectable in the range of 20-30 cm. The high energy threshold is an optimization parameter that determines whether the treatment plan generated is a single energy treatment plan or a mixed energy treatment plan. This threshold defines the separation value to convert a treatment plan from a single energy treatment plan to a mixed energy treatment plan, in order to help improve dose homogeneity in patients with large separations.

The separation on each treatment slice for a particular gantry angle, collimator angle and isocenter position is determined. If the separation is greater than the threshold, a mixed energy plan is automatically selected with a primary beam at low energy (i.e., nominal energy) and high energy for beam segments. The low energy beam may produce an unmodulated field while the high energy beam may produce a modulated field. The user may be provided with an option to select this threshold value directly.

The clinical requirement(s) may also be predefined in the system, for example preset by the user prior to 802 or coded as a default in the system. For example, certain common or threshold parameters may be predefined for certain types of treatment planning.

Additionally or alternatively, the user may be provided with a list of selectable predefined sets of clinical requirements (e.g., a certain set of parameter values may be common for treatment of certain tissues, such as the breast, and this may be a predefined set that is selectable by the user, for convenience).

The user may be provided with standard clinical considerations (which may be presented as clinical questions), such as how much non-target tissue should be allowed in the treatment field, what should be the margin on the post-surgical cavity, and what is the shielding to be added. The clinical requirement(s) may be determined using the user's response to these clinical considerations. These clinical considerations may be predefined and may be different depending on the application (e.g., whether treating breast, prostate or head and neck).

Any clinical requirement that is not specified by the user may be assigned a predefined default value.

At 806, one or more technical parameters are calculated to satisfy the clinical requirement(s). Calculation of the technical parameter(s) may include determining one or more optimization parameter(s), using a predefined empirical rule/relationship, to be used in an optimization algorithm.

The system may automatically calculate all necessary technical parameters for the treatment plan while ensuring that the clinical requirement(s) are met. This automatic calculation may include, for example, determining treatment beams, dose-volume objectives based on the anatomy, and other treatment planning related activities (e.g., all activities that may be conventionally manually done).

These calculations may be based on one or more empirical rules/relationships, such as those implemented using the lookup tables and curves described below, or other empirical rules/relationships that may be implemented in other lookup tables, curves, statistical models, machine learning models and other suitable techniques.

Figure 11A:
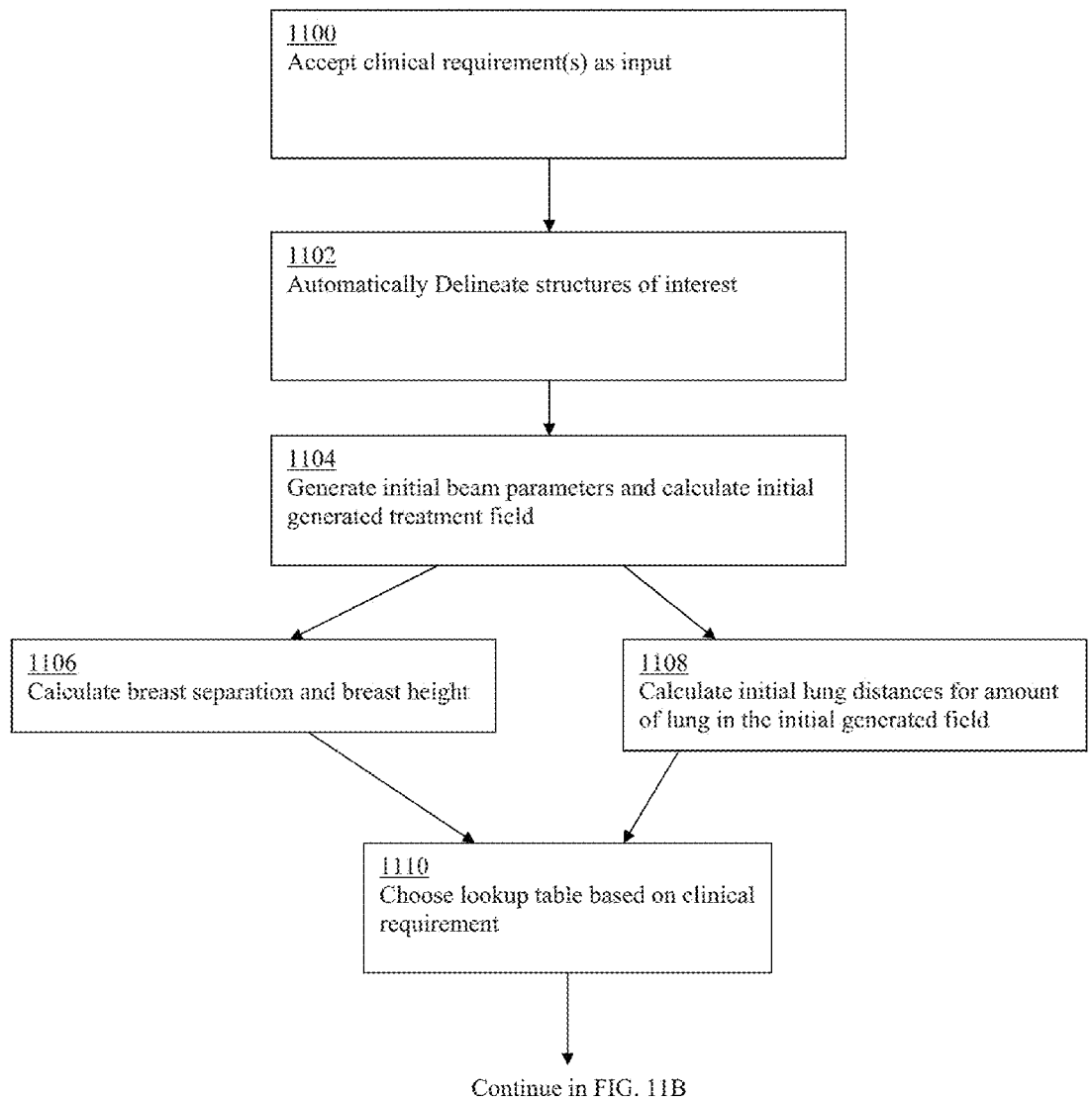
FIGS. 11A-11C shows a flowchart illustrating an example method for automated optimization of technical parameters using empirical information.
Figure 11B:
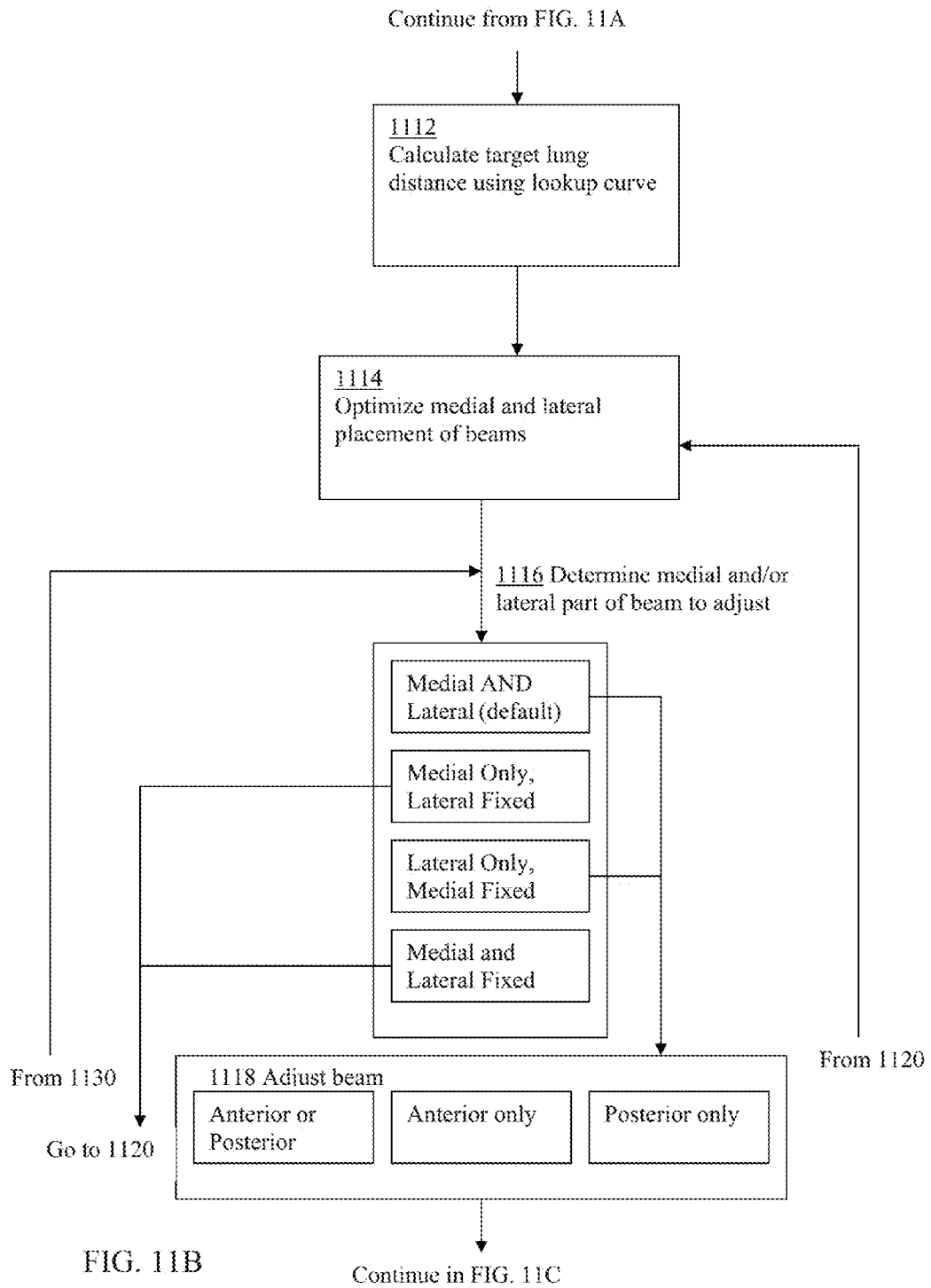
Figure 11C:
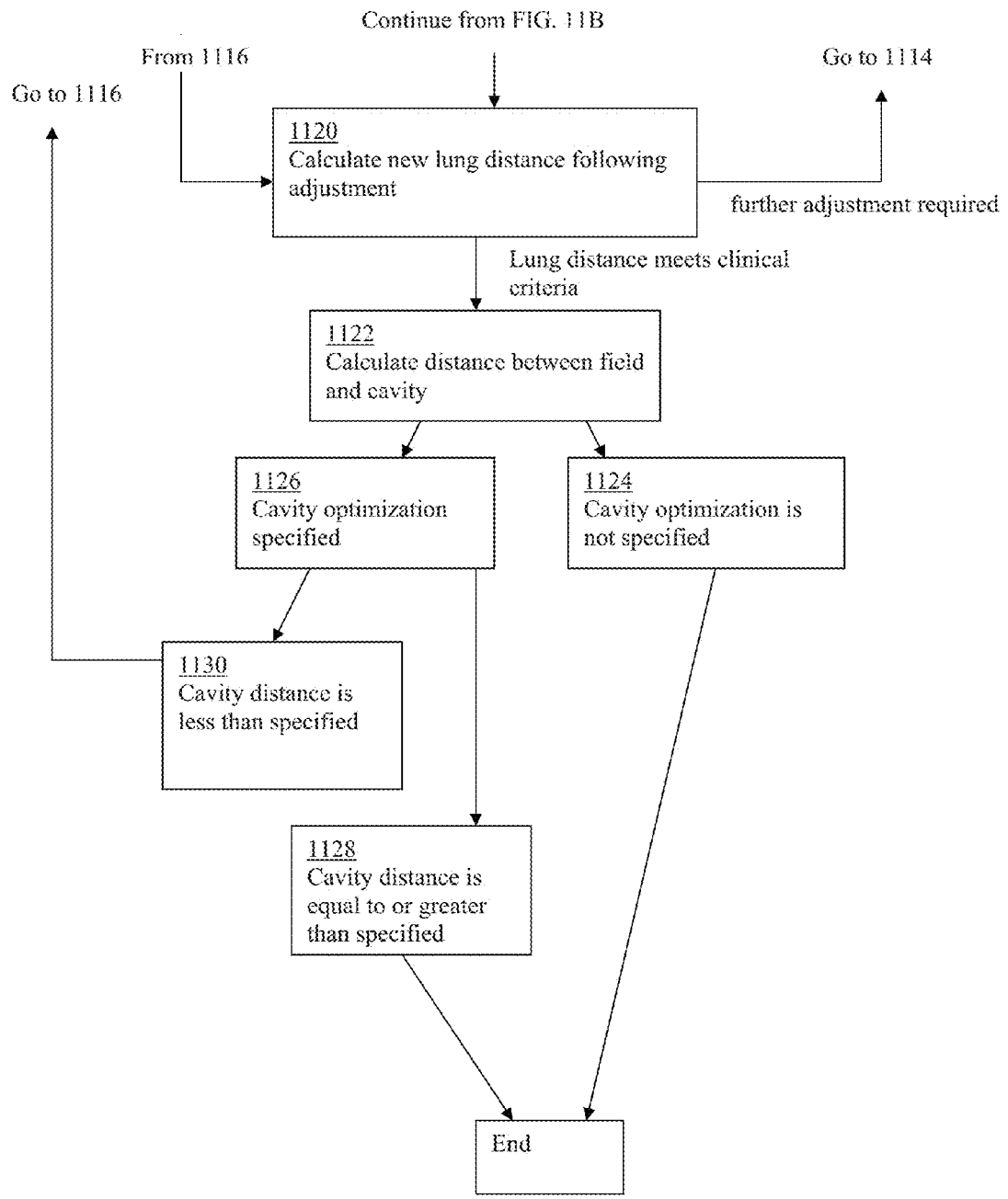

The automated calculation of the technical parameters may be carried out using the example method of FIGS. 11A-11C.

The flowchart in FIGS. 11A-11C illustrates an example method for optimization for beam placement (e.g., optimization of gantry angle, beam isocenter placement and collimator angles). Although this example refers to calculation of a treatment plan for treatment of breast tissue, a person skilled in the art would understand that similar steps, with suitable variations (e.g., different target and non-target tissues, and different markers), may be used for planning treatment of other target tissues.

At 1100, one or more clinical requirements are accepted as input. As described above, the clinical requirements may be any requirement selected by a clinician or oncologist, such as those described elsewhere in this disclosure. One or more of the clinical requirements may also be preset in the system as default selections.

At 1102, information identifying the delineated structures of interest is received. The structures of interest, in the case of treatment of the breast, may include: the lungs, the heart, the wire outlining the breast (e.g., obtained from CT simulation), tissues inferior to the diaphragm, and the humerus.

This may be carried out using automatic delineation, as described above. For treatment of breast tissue, structures of interest may include the lungs, heart, wire outline of the breast (e.g., from CT simulation), tissues inferior to the diaphragm, and the humerus. Other structures may be identified for different applications.

At 1104, initial beam parameters are generated based on nominal values or general targets, to create an initial candidate treatment plan. The resulting treatment field that would be generated is also calculated. For example, the initial beam parameters may specify a gantry angle and isocenter that passes through the reference geometry (e.g., for the case of treatment of the breast, passing through the breast markers). The collimator angles may be specified so that the beam is parallel to the length of the identified lung in a 2D projection of the beam. The initial beam parameters may be used to calculate the initial breast size for optimization.

For example, the initial beam parameters may correspond to the anatomical markers locations, such that the medial aspect of the beam may pass through the medial point and the lateral aspect of the beam may pass through the lateral point. The isocenter may be placed on the line connecting these points with the lateral position of the point determined by the sagittal plane containing the superior and inferior points. Based on the initial beam, initial tissue parameters (e.g., the volume of lung and normal tissue within the beam) may be automatically scored and may be expressed, for example, as a mean and maximum lung distance.

At 1106, the actual breast separation-height (i.e., product of breast separation and breast height) is determined. This may be calculated from the delineated structures, or may be inputted by the user. The breast separation-height value may be used to determine a breast size correction factor when determining an optimization parameter from a lookup table, such as Table 2 of FIG. 14 described elsewhere in the present disclosure.

At 1108, the initial lung distance is calculated for the amount of lung in the calculated treatment field, based on the initial beam parameters. This may be done by calculating the mean and maximum lung distances (cm) in the initially generated treatment beam. For each point in the delineated lung volume, the distance from the point to the edge of the treatment area is calculated. The average of all these distances is calculated to obtain the mean lung distance, and the maximum of all these distances is calculated to obtain the maximum lung distance. The calculated mean lung distance and maximum lung distance may be used when determining an optimization parameter from a lookup table, such as Table 2 described elsewhere in the present disclosure.

At 1110, an empirical lookup table is selected from one or more predefined lookup tables (e.g., Table 2) stored in the processor. The lookup table may be used to determine an optimization parameter based on an empirical lookup curve. In this example, the optimization parameter is the target lung distance that the automated calculations should use as the end goal of optimization. Because the appropriate empirical lookup curve may be different depending on whether it is desired to cover more or less lung tissue, different lookup tables may be used. In this example, four empirical lookup tables are available: for a user-defined lung distance, for a pre-defined "less lung" distance, for a pre-defined "more lung" distance and for a pre-defined "nominal lung" distance.

For example, Table 2 illustrates and example empirical lookup table for determining the target lung distance for a "nominal lung" selection. The "more lung" and "less lung" lookup tables may contain values that are increased or decreased, respectively, from the nominal values. The pre-defined "more lung", "less lung" and "nominal lung" values may be preconfigured in the system (e.g., at installation). The different combinations of breast size correction, more/less/nominal lung and mean or maximum lung distances result in a number of different empirical lookup curves from which the suitable lookup curve is automatically selected, in this example.

At 1112, the selected lookup table is used to determine coefficients to be used in a lookup curve for calculating the optimization parameter, in this case the target lung distance. The target lung distance is calculated based on the empirical relationship modeled by the lookup curve.

Table 2, for example, provides coefficients to be used in an empirically determined lookup curve that may be used to calculate the target lung distance for use as an optimization parameter in an optimization algorithm. The appropriate coefficients in Table 2 are automatically selected by the system based on the value of the initial lung distances calculated from the initial generated field (as calculated in 1108 above), whether the clinical requirements specify a mean or a maximum lung distance, and whether breast size correction (e.g., based on the breast separation-height value as calculated in 1106 above) is required.

At 1114, the medial and lateral placements of the beams are optimized to fit the user-specified clinical requirements. This optimization may include optimization calculations using the empirically determined optimization parameter, described above. The technical parameters to be optimized may include the gantry angle, the beam isocenter position and the collimator angle.

The optimization in this step may involve iteratively changing the angle of the gantry and moving the isocenter, for example, to achieve the optimization parameter, in this case the target lung distance. After each adjustment, the generated field as well as the lung volume in the newly generated field is re-calculated for the new candidate treatment plan. At each re-calculation of the lung volume, an optimal collimator angle which minimizes the amount of lung in the treatment field is determined. The result of this optimization may be a collimator that is oriented parallel to the shape of the lung.

At 1116, adjustment of the beams may involve: medial and lateral adjustments (this may be the default setting unless the user specifies otherwise); medial adjustments only; lateral adjustments only; or neither medial nor lateral adjustments permitted. The user may input these limits on the adjustment of the beams as constraints on how optimization may be carried out. For example, in addition to meeting the target lung distance as determined from an empirical lookup table, optimization calculations may also take into account any boundary conditions set by the user. Thus, the target lung distance, as well as any medial and/or lateral beam constraints may be taken into account during optimization.

At 1118, if the user-specified clinical requirements allow the lateral beam to be adjusted, then it is determined whether the user has specified the lateral beam to be adjustable anteriorly and posteriorly; anteriorly only; or posteriorly only. The beams may then be adjusted according to these user-specified limitations. If the user-specified clinical requirements require the lateral beam to be fixed, this step may be bypassed.

At 1120, after beam adjustment, the lung distance is recalculated. If the lung distance satisfies the user-specified lung distance requirement, then the method proceeds to 1122. If the lung distance does not satisfy the user-specified lung distance requirement, the method returns to 1114 to further optimize the beam parameters. Typically, each time the gantry angle is adjusted, a new isocenter position is calculated and the collimator is re-optimized.

At 1122, the margin distance between the outer edge of the treatment field and the outer edge of the post-surgical cavity is calculated. A clinical requirement that may have been specified is cavity optimization. Cavity optimization may be selected by the user to ensure that the entire post-surgical cavity is included in the treatment field and the amount of margin for inclusion. If cavity optimization has not been specified as a clinical requirement, this step may be bypassed. In some examples, if the cavity has not been delineated, this step may be bypassed and the user option for specifying cavity optimization may be disabled.

At 1124, if the cavity optimization requirement has not been specified in the inputted clinical requirements, the method ends and optimization of the technical beam parameters is complete.

At 1126, if the cavity optimization requirement has been selected by the user, it is determined whether the calculated cavity distance, defined as the distance from the outer edge of the treatment field to the outer edge of the post-surgical cavity, is less than or equal to/greater than the value specified by the user.

At 1128, if the calculated cavity distance is equal to/greater than the value specified by the user, the method ends and optimization of the technical beam parameters is complete.

At 1130, if the calculated cavity distance is less than the value specified by the user, the method returns to 1116 to adjust the medial and lateral beam parameters. Because the method returns to 1116, this adjustment does not adjust any values based on the target lung distance as in 1110-1120. That is, cavity optimization may be prioritized over optimization of lung distance.

Once the beam optimization described above is complete, shielding values may be considered, based on user-specified shielding values. For example, once the gantry angle, isocenter position and collimator angle values are optimized, such as described above, the beam shielding for the primary beam segment may be calculated based on any user-specified shielding clinical requirements. For treatment of breast tissue, shielding for the segmented volumes for non-target tissues such as the heart, the humerus and tissues inferior to the diaphragm may be automatically determined. In the example treatment of breast tissue, the gantry angle, isocenter position and collimator angle optimization typically may be carried out based on the lung volume, therefore shielding for these other non-target tissues may not affect the optimized gantry angle, isocenter position and collimator angle values. In other applications, such as other target tissues, or for treatment of breast tissue where additional shielding is applied to the lungs, shielding may require further adjustment of gantry angle, isocenter position and collimator angle values, for example using a variation of the optimization described above. For example, where the method includes shielding optimization, such optimization may take place after cavity optimization (and/or wire optimization, as described below), and the method may return to determination of target lung volume after shielding optimization. In some examples, shielding optimization may be included in every iteration where the gantry angle and isocenter position are changed.

Additionally, wire optimization may be incorporated into the optimization method described above. Wire optimization may be incorporated as is conventionally done in manual treatment planning methods. For example, the steps for wire optimization in the example method described above may be similar to the steps described above for cavity optimization and may be carried out following cavity optimization (if selected). In some examples, cavity optimization may be carried out by default but not wire optimization. Where the user has specified that wire optimization should be carried out, wire optimization may require the wire marker to be delineated in the image data. Wire optimization may be disabled where there is no wire marker in the image data.

Although in the example above, cavity optimization and/or wire optimization have been described as taking place after determination of the target lung volume from a lookup table, it should also be understood that cavity optimization and/or wire optimization may take place prior to determination of the target lung volume. The order of cavity optimization and wire optimization may also be varied. The cavity optimization and/or wire optimization in this example takes place after determination of the target lung volume, and the target lung volume is not rechecked after cavity optimization. In other examples, the target lung volume may be rechecked after cavity optimization and/or wire optimization.

The automated method may also include other calculations. For example, in a breast treatment plan, a Treated Volume may be defined based on the automatically determined configuration of the radiation beams. For example, the Treated Volume may be defined as the volume of tissue irradiated by the beams at the 55% isodose level (1). However, this Treated Volume may encompass critical non-target organs such as heart, liver and the ipsilateral lung, which may be defined as an Avoid volume. Therefore, the target Breast volume may be defined as the Treated Volume excluding the Avoid volume, although non-breast tissue (such as muscle and fat tissue) may still be included in the defined Breast volume, as may be the case for conventional tangent radiation therapy of the breast.

The automatic calculation may contract the Breast volume, for example using empirical rules developed from treatment plans for similar target tissue, in order to avoid radiation to the skin surface. For example, an empirical rule may be pre-defined to contract the Breast volume by 5 mm in the axial plane and 10 mm in the superior-inferior direction. This empirical rule may be based on practice commonly done in IMRT treatment planning (1). The calculations may also automatically modify the cavity volume to define the optimized cavity volume as the delineated post-surgery cavity volume excluding any tissue outside the optimized breast volume.

Other such empirical rules/relationships may be implemented in the automated calculations.

Returning to FIG. 8, at 808 the calculated treatment plan (e.g., optimized according to the method of FIGS. 11A-11C) may be stored and/or transmitted for use in clinical treatment. For example, the treatment plan may be stored in a memory or database in the system for later retrieval and/or modification (e.g., manual fine-tuning). The treatment plan may also be retrieved in the future as a basis or template for other automated treatment planning.

In some examples, the calculated treatment plan may also include a quality assurance tool that may provide the user with feedback about one or more facets of the plan generated. For example, feedback may include details of one or more physical plan parameters related to the beams and/or the dose they are delivering, in addition to clinical details about the plan. The feedback may also include a dose volume evaluation which may report on the dose to relevant ROIs and/or may compare the doses both the target and normal tissue ROIs received, for example as compared with certain clinical and/or user-specified criteria (e.g., safety thresholds).

FIGS. 12A-12B show an example of a quality assurance report that may be automatically generated after the treatment plan has been automatically calculated. In this example report, calculated values of the treatment plan (e.g., amount of lung distance, beam parameters, and calculated expected dosages) are displayed along with the typical or average value, indicated as "Limit", for comparison. The "Limit" value may be based on values that have been commonly used in the past, or based on clinical policies, and may allow the user to identify any values that may be considered unusual or unexpected. Values that are outside of the "Limit" value may be flagged to alert the user, but may still be clinically acceptable and/or desired by the user despite being outside of the nominal value range.

An example of the operation of the automated method is described below.

In this example, the user may input, as a clinical requirement, fixing the beam to the medial marker and specifying that having more lung in the treatment beam is clinically acceptable.

Based on these clinical requirements, the automated calculations are constrained to calculate gantry angles such that the medial part of the beam fixed at the medial marker and only allowing for adjustment of the lateral part of the beam. An empirical lookup table may be used to determine the target lung volume for iterative optimization of the beam. At each iteration, the amount of lung coverage is calculated. The treatment fields are iteratively adjusted only on the lateral side. For example, if the treatment field should be shallower on the patient, the isocenter position may be automatically adjusted up; if the gantry angle needs to be steeper, the isocenter position may be automatically adjusted down. The automated method iterates through such adjustments and checking of resulting lung distance until the target amount of lung distance is achieved while still adhering to any other constraint set by the user with respect to the allowable range of placement of the beam. The values of the gantry angle, isocenter position and collimator angle that satisfies this target are stored.

The automated method may then consider whether cavity optimization is satisfied, that is whether the specified cavity margin is achieved. Since the user has not specified a value in this example, the default margin value of 1.0 cm may be used. If the distance from the outer edge of the treatment field to the edge of the cavity is greater than the specified margin, then cavity optimization is satisfied and the calculated values for the gantry angle, isocenter position and collimator angle are finalized for the treatment plan. If the specified margin is not satisfied, then optimization of the beam parameters is repeated, as described above, until the cavity margin is satisfied.

Any shielding specified by the user may then be considered by the automated method. The addition of shielding typically does not affect the optimized gantry angle, isocenter position and collimator angle values. Shielding may be achieved by adjusting the multileaf collimator to shield the relevant structures, according to clinical requirements for shielding in the primary beam segment. Specified shielding does not affect the number of segments or the segment area, which are typically set based on the target volume.

In the above example, the user specification of a fixed lateral beam position constrains which parts of the beam may be adjusted in the automated method and/or the range of permissible adjustment. The lung volume calculation determines which empirical lookup table should be used. The optimization of beam parameters (i.e., the gantry angle, isocenter position and collimator angle) is typically overridden by cavity optimization, unless otherwise specified by the user.

Although not described in this example, wire optimization may place additional constraints on the automated method by setting margins for coverage of the wire and thus may take priority over optimization based on the target lung distance determined using an empirical lookup table. As explained above, wire optimization may be carried out similarly to cavity optimization.

As illustrated in the above example, although the user may specify different independent clinical requirements, satisfying one requirement requires the automated method to perform adjustments of beam parameters that may affect whether another requirement is satisfied. The larger the number of clinical requirements specified, the more difficult it may be to satisfy all clinical requirements and the higher the chance that no satisfactory treatment plan can be generated.

The disclosed methods and systems for automated treatment planning may be integrated into conventional clinical treatment planning systems (e.g., Pinnacle3, Philips Radiation Oncology System). For example, the disclosed methods and systems may replace conventional manual trial-and-error planning steps or a semi-automated method.

The disclosed methods and systems for automated treatment planning may provide a relatively simple (e.g., "one-click" method) for planning radiation therapy. The disclosed methods and systems may automatically generate a treatment plan based on the clinical requirements of the user, without requiring extensive experience or technical knowledge from the user, nor trial-and-error modification of the treatment plan. The disclosed methods and systems may provide for automated determination of the technical parameters for a treatment plan based on clinical requirements.

Example Study

An example study of an example embodiment of the disclosed methods and systems for automated treatment planning is now described. This is for the purpose of illustration only and is not intended to be limiting. The present disclosure is not limited by the methods, results or details described in any examples provided.

In this example, automated treatment planning for treatment of breast tissue was carried out using a conventional clinical treatment planning system (e.g., Pinnacle3, Philips Radiation Oncology System). In this example, the automated treatment planning method was used to automate the manual volume delineation, beam placement and IMRT treatment planning steps conventionally carried out manually by the treatment planning radiation therapist. The technical parameters automatically calculated in this example include the beam gantry and collimator angle, and the size of the beam apertures used for treatment.

In this example, radio-opaque markers identified during CT simulation were provided as inputs, tangential beam parameters were calculated to geometrically reduce or minimize the amount of lung and heart tissues (i.e., the non-target tissues) treated while covering most or all of the whole breast volume (i.e., the target tissue). IMRT parameters were calculated based on the automatically delineated whole breast volume.

In this example study, a total of 158 planned patients with Stage 0, I, and II breast cancer treated using whole-breast IMRT were retrospectively re-planned using an example embodiment of the automated treatment planning methods and systems described above. Clinical treatment plans with mixed photon energy beams (n=6) and beam geometries which included the treatment of the contra-lateral breast (n=4) were excluded from the analysis.

CT Simulation

In this example, images of the target treatment volume were acquired using CT scans using a conventional Philips Large Bore CT scanner. Patients were set up in the supine position on a breast board (from MedTec, Orange City, Iowa). In these scans, the arm on the treated side was raised on the arm support to achieve an angle greater than 90 degrees to the patient's body. The arm on the contra-lateral side was rested at the patient's side. In this example study, the anatomical markers used included four radio-opaque markers and a radio-opaque wire placed on the patient (e.g., according to conventional clinical processes for identifying breast tissue and for providing landmarks to be used at the treatment unit).

An example CT image is shown in FIG. 1. The top left image is an example axial CT image from CT simulation scan with radio-opaque markers placed at the time of simulation. The top right image is an example view from the perspective of the medial treatment beam showing the area to be treated. The example view shows the outline of non-target volume (in this case, the left lung volume) and the target treatment volume (in this case, breast tissue) to be treated. In this example, these structures were automatically delineated as part of the automated treatment planning method. The bottom image shows an example surface rendering of a patient, showing the medial (A), lateral (B), superior (C) and inferior (D) markers and the medial tangential beam projected on the patient's surface (white). A breast wire is also shown.

In this example, radio-opaque markers placed at the time of CT simulation were as follows: A) the medial marker (in this case, 1.0 cm medial to the breast wire, which does not cross midline; B) the lateral marker (in this case, 1.5 cm posterior to the wire around the breast, midway between the superior and the inferior markers); C) the superior marker (in this case, 1.5 cm superior to the breast tissue or the level of supra-sternal notch (whichever is more superior) which may include all visible tissue); and D) the inferior marker (in this case, 1.5 cm below the infra-mammary crease or the lower part of the breast (whichever is more inferior) which may be in the same sagittal plane as the superior marker).

In this example, the automated treatment planning method automatically determined the location of these landmarks. This may be done using any suitable methods.

Automated Treatment Planning

The disclosed automated methods for treatment planning may be implemented on a conventional system used for conventional manual treatment planning (e.g., the Pinnacle3 treatment planning system on the standard 810 hardware running Solaris 10). In contrast with the manual approach, the disclosed automated methods and systems incorporates the experience of multiple clinicians over multiple treatment plans in the form of empirical rules and lookup tables, such that an inexperienced user would benefit from the experience of past clinicians and produce a treatment plan similar to an experienced user, without the inexperienced user having to understand all the complicated technical parameters and underlying relationships between the clinical requirements and the technical parameters.

The automated planning method may be carried out using conventional software. In this example, the automated planning method was implemented using both the inherent Pinnacle3 scripting language and the Python scripting language (Version 2.3.3), which may be included with the operating system. This may allow the automated planning method to be implemented on any conventional system available (e.g., any Pinnacle system), without any installing additional hardware or software.

In this example study, automated treatment planning was carried out using as input the four anatomical points described above, with the breast wire defining the breast tissue, and the lung and normal tissue volumes. The automated method automatically located the markers corresponding to the medial, lateral, superior and inferior extent of the breast, and defined a point of interest for each marker. In addition, the method determined the apex of the breast on the isocenter slice to define an anterior point. The anterior point was used to calculate an appropriate anterior jaw setting (in this case, including 2 cm of skin flash). In addition, the radio-opaque wire outlining the breast tissue was automatically extracted to define a region of interest volume.

In this example, the automated algorithm automatically delineated the ipsi-lateral lung, contra-lateral lung and heart, using a combination of image threshold methods and multiple levels of model-based segmentation (MBS) adaptation (which may be a module provided by the example treatment planning system). Adaptation using MBS may generate organs as three-dimensional polygonal surface meshes, which may be defined by a collection of vertices. Following adaptation, theses meshes were then converted to Cartesian co-ordinates to define region of interest volumes. The diaphragm and the normal tissue inferior to the diaphragm (in this case the liver, spleen and stomach), was also delineated (e.g., using threshold methods) as a single volume. The target volumes for the automated plans were automatically generated using the techniques described above.

In this example, empirical rules were used to calculate certain IMRT optimization parameters, such as the maximum number of segments and the minimum segment area, according to the target volume. These optimization parameters were determined using an empirical lookup table, in this example Table 1 of FIG. 13. The values in Table 1 were empirically developed from a database of previous treatment plans and results. For example, empirical data and/or relationships may be extracted from existing information about treatment plans (e.g., from a database of historic radiation treatment plans and outcomes) that may be kept on record by a hospital or other treatment facility.

These values were developed to avoid excessive beam modulation and treatment delivery complexity (i.e., avoiding too many small segments) while providing sufficient latitude for the optimization algorithm to calculate the segmentation required to reproduce the optimized fluence.

In this example, Table 1 was generated empirically based on numerous (e.g., 1000 or more) previously done treatment plans and outcomes. The number of segments and the segment area required to generate an acceptable treatment plan were considered. In the example of Table 1, based on previously obtained treatment plan data, it was found that larger target volumes were typically better treated with more field modulation but typically did not require small area segments. Conversely, for smaller target volumes, it was found that typically many smaller segments were better for achieving does objectives and for proper optimization of IMRT parameters. These findings were converted to empirical rules and stored as empirical values in Table 1. Other such empirically determined rules may be stored in other lookup tables.

As well, the robustness of the previously generated plans was considered. The number of segments defines the level of modulation allowed in the treatment field. As the number of segments increases, the modulation increases. The segment area defines the minimum area that an individual segment can have. The lower the minimum area, the smaller the possible segments generated and hence larger numbers of segments are possible, resulting in potentially more modulation. Conversely, as the segment area value is increased, the generated plans have the potential for less modulation since larger and hence smaller numbers of segments are generated. However, using larger segment area values risks poorer or failed optimizations because the optimization parameters may become too constrained.

Depending on the segment area and number values, the IMRT optimization algorithm may not be able to generate an optimized treatment plan. Accordingly, the values in Table 1 were also selected so that treatment plans may be produced with as little complexity in terms of modulation as possible.

In other examples, optimization parameters may be determined using empirical lookup curves. These curves may be modeled based on data gathered from records of previous patient treatments.

Table 2 illustrates an example of an empirical relationship that may be used in the disclosed methods and systems. Table 2 provides a map of the empirical relationship between the user-specified treatment field coverage and the target lung distance to be achieved.

Table 2 may be calculated based on numerous (e.g., 1000 or more) previous treatment plans and outcomes. In the example of Table 2, the empirical relationships provided by the table is based on the initial lung distance calculated for the initial candidate beam parameters (e.g., as described for 1108 of FIGS. 11A-11C, above). Determination of the empirical relationships of Table 2 may involve back-calculating the initial lung distance for a large number of previously generated treatment plans and relating this to a forward-calculation of the final lung distance achieved. The results of these time-consuming and expensive calculations have been defined as an empirical relationship in Table 2, such that any user using the disclosed automated methods and systems may benefit from such empirical knowledge.

For Table 2, the initial lung data was fitted using a simple log equation, which had a high correlation co-efficient with the fit. Different versions of Table 2 may be used based on the specific patient. For example, in treatment of the breast, the patient may be categorized based on the patient's breast shape (e.g., defined by the length and the height of the breast) and the appropriate lookup curve may be automatically selected based on the target treatment volume.

For example, in the model of Table 2, it was found that to accommodate a small breast (i.e., separation-height <200 $cm^2$), a different lookup table was required compared to a large breast. An initial set of beam parameters may be calculated, corresponding to the anatomical markers and the initial mean lung distances calculated to look up the target lung distance for optimization of the gantry angle (e.g., as described above with respect to FIGS. 11A-11C).

In Table 2, for initial mean lung distances between 1.3 and 1.5 cm, the initial gantry angle may be selected without any further optimization. In this example, breast size correction may be based on a product of breast separation and breast height of initial gantry angle.

In this example, the optimal gantry angle may be automatically determined, for example by scoring the normal tissue volume within the field at various gantry angle/isocenter combinations until the clinically acceptable target mean and maximum distances are achieved. Typically, for maximum lung distance, 1.5 cm of lung is considered acceptable in a treatment plan, and a range of 1.0-2.0 cm is typical. For mean lung distance, a value of around 1.0 cm is typically considered acceptable, and values typically fall in the range of about 0.7-1.6 cm. The disclosed methods and systems may offer a way to calculate or measure these lung distance values, whereas these values typically are not readily apparent in conventional treatment planning. The medial and/or the lateral aspects of the beam may be optimized from the initial beam placed on the anatomical points.

For example, the beam may be optimized to allow the medial aspect of the beam to move toward the breast wire while preventing the medial part of the beam from moving toward the contra-lateral breast. For example, the lateral aspect of the beam may move either anterior to the lateral point to decrease the normal tissue volume in the beam or posterior to the lateral point to increase the normal tissue volume within the beam. User-specified clinical constraints may constrain the amount of adjustment during optimization.

The gantry optimization may include optimization of the cavity volume, where the cavity has been delineated. For example, the method may automatically create a geometric margin for the cavity, which may be specified as the minimum distance between the outer edge of the cavity and the beam outer edge. In this example, a default minimum distance of 1.0 cm may be used for generating the automated plans. This default value may be selected based on a conventional clinical treatment planning protocol.

For each iteration of the gantry optimization, the automated treatment planning method may iterate through each collimator angles step-wise and may calculate the two-dimensional mean and maximum normal tissue distance in the beam eye view (BEV) projection at the given gantry angle. The angle corresponding to the minimum two-dimensional distance for the given gantry angle may be selected as the optimal collimator angle. The algorithm may include only collimator angles which encompass the breast wire.

The distance between the wire and the field edge may be scored and only collimator rotations which result in beam apertures with the minimum breast wire distance greater than zero may be included in the collimator angle optimization. This empirical rule may help to ensure that the collimator is not rotated excessively such that the wire (i.e. the marker representing the position of the breast) falls outside the treatment field. This constraint helps to keep the collimator angle within clinically acceptable limits, and is typically in the range of 5-25 degrees.

The disclosed automated treatment planning method may be used to optimize all IMRT parameters. IMRT parameters may be automatically determined according to the target volume, for example. The maximum number of segments and the minimum segment area for optimization may be constrained according to the size of the target volume, for example based on empirical values, which may be stored in a lookup table.

In this example study, the mean time to generate a complete treatment plan was found to be relatively quick (e.g., on the order of 5 to 7 minutes).

For developing the empirical rules/relationships, such as those embodied in lookup tables and lookup curves, used to relate a desired clinical requirement to optimization of the technical parameters empirical data from previous treatment plans are used. Empirical data such as breast separation, lung distance, etc. may be readily available or extractable from records of historic treatment plans.

The lookup tables and lookup curves, such as provided in Table 1 and Table 2, may be continuously refined by incorporating additional data on previous treatment plans and outcomes. The more data on which such empirical tables are based, the more accurate and widely applicable these tables may become.

As new data is added to a treatment plan database, one or more empirical rules may be updated to incorporate the new data. This update may be carried out periodically or at each update of the raw data. Treatment plans that were developed using the disclosed automated treatment planning methods and systems may also be included in the database and be used to update the empirical rules.

Although the disclosed methods and systems is capable of generating a treatment plan automatically, without manual adjustment of the technical parameters, one or more options for manual adjustment may still be provided to the user.

Conventional Manual Treatment Planning

For comparison, treatment planning using an example of conventional manual methods was also performed.

Treatment planning was completed using a conventional treatment planning system, in this case the Pinnacle3 treatment planning system (e.g., v8.0d, Philips Radiation Oncology Systems, Fitchburg, Wis.). An example conventional treatment planning process was carried out based on the work published by William Beaumont Hospital (1). This conventional planning required the radiation therapy treatment planner to create medial and lateral tangential treatment beams with a matched posterior non-diverging border (i.e. half-beam block), and field size extension at the apex of the breast (i.e. skin flash), to account for breathing motion. The operator may manually adjust the gantry angle, collimator angle (to follow the lung-chest wall interface), jaw positions, shielding and beam isocenter to achieve coverage of the clinically defined breast.

In this example study, conventional manual treatment planning included manual volume delineation. The clinician may be required to manually delineate the ipsi-lateral lung, contra-lateral lung, the heart and any critical organs (in particular the liver and spleen). These critical organ volumes may define the Avoid volume (i.e., the volume that is preferably avoided by the treatment beams). A radiation oncologist may delineate the post-surgery cavity (seroma) provided the cavity was clearly visualized and this may influence the beam geometry. In this example study, the cavity was manually delineated in 58 of the 158 plans.

In this example study, the target volume for optimization was generated based on the beams manually placed by the planner, for example using an approach consistent with that previously described by Vicini et al (2). The manual placement of treatment beams typically involves trial-and-error. The Treated Volume may be defined as the volume of tissue irradiated by the planner-generated beams at the 55% isodose level. The Breast volume may be manually adjusted to define the Treated Volume to exclude the Avoid volume (e.g., heart, liver and the ipsilateral lung). In some examples, the Breast volume, may be further adjusted to define an optimized breast (OptBreast) volume contracted a given amount (e.g., by 5 mm in the axial plane and 10 mm in the superior-inferior direction), to exclude skin tissue. The cavity volume may also be manually modified to define the optimized cavity (OptCavity) volume as the delineated post-surgery cavity volume excluding any tissue outside the OptBreast volume.

The step and shoot conventional manual IMRT planning approach was used to help ensure that the manually generated beams are at or near the highest weighted segment following optimization. In this example, each of the medial and lateral planner-generated tangential beams was copied, so there were four beams in the IMRT optimization. However, the beam weightings were set such that the beams each initially may contribute, for example, 49% of the overall beam weighting prior to optimization.

In this example, the manually generated beams were manually optimized for beam weight (e.g., using trial-and-error, or with the assistance of scripts provided in the treatment system). The copied beams were subject to a fully-inversed IMRT optimization, but retain the isocenter, gantry angle and collimator angle of the manually generated beams. Therefore, the manually generated beams were invariant except for the beam weight as determined by the optimization and the copied beams were effectively an electronic compensation using segments generated by the optimization in an inverse-planned approach. In this example, a direct aperture methodology called direct machine parameter optimization developed by RaySearch Laboratories (Stockholm, Sweden) and included in the Pinnacle3 RTP system was employed for the optimization (10)(11).

Following optimization of the four beams, the manually generated beams were inserted into the corresponding segmented beam as the first segment, restoring the plan to only two beams. This approach was used to help ensure that the manually defined beam, which includes flash, was always included in the plan and the manually defined aperture also contributed the highest weight (e.g., 75-85% of the overall beam weight) as beam weighting were biased to the manually defined field prior to optimization, as described above.

The manual approach to treatment planning often takes an hour to several hours to carry out, and many involve multiple trial-and-error iterations. The experience and intuition of the clinician is a significant factor in the manual approach, making such an approach very user-dependent and not easily replicable by other clinicians. Further, the manual approach does not go through all the methodical steps of the automated method, as in the example described above, and to do so would take an extremely long time and be very prone to error.

Comparison of Conventional and Automated Treatment Planning

In this example study, plan parameters, beam parameters and dose-volume data for target volumes and normal tissue volumes were recorded to facilitate comparison between the automated and manually generated plans (also referred to as clinical plans). The results were compared for statistical significance using a paired t-test. In addition, the optimized breast target volumes generated using the automated planning algorithm and target volumes generated from the clinical plans were scored for agreement. The target volume overlap was measured as the ratio of the intersection of the two target volumes to the union of the two volumes. A fraction volume overlap of 1.0 indicates that the two volumes completely overlap while a volume overlap of 0.0 indicates that there is no overlap. The Hausdorff distance, a strict segmentation metric to assess the mismatch between two volumes as a vector distance, is defined as the maximum of the minimum distances for each point between two volumes (12). The smaller the value of Hausdorff distance, the smaller the mismatch between the two volumes.

In this example study, the treatment plans generated by the automated treatment planning method were scored for clinical acceptability by one experienced breast radiation oncologist (R.E.D.). For each patient, the automated and clinical plans were anonymized and randomized in a double-blinded study. The radiation oncologist reviewed the anonymized plans side-by-side in the treatment planning system. The 158 clinical plans were previously reviewed by 10 different radiation oncologists, 5 different radiation physicists and created by 9 different radiation therapy planners (dosimetrists). Each of the anonymized plans were evaluated based on the maximum plan dose, the dose homogeneity in the whole breast volume, minimum dose to the whole breast, minimum dose to post-surgery cavity (if delineated) and dose to critical structures: heart, ipsilateral lung and contra-lateral breast. In addition, the radiation oncologist either approved or rejected the plan for clinical acceptability based on all of the above criteria.

The results show that for the plans generated using the automated treatment planning method, 157 of 158 (99%) plans were deemed clinically acceptable and 138 of 158 (87%) plans were deemed clinically improved or equal to the corresponding clinical plan when reviewed in a randomized, double-blinded study by one experienced breast radiation oncologist. In addition, automated plans were equivalent to the clinical plans when scored for target coverage, lung and heart doses and in the delineation of the whole breast target volume.

Figure 3:
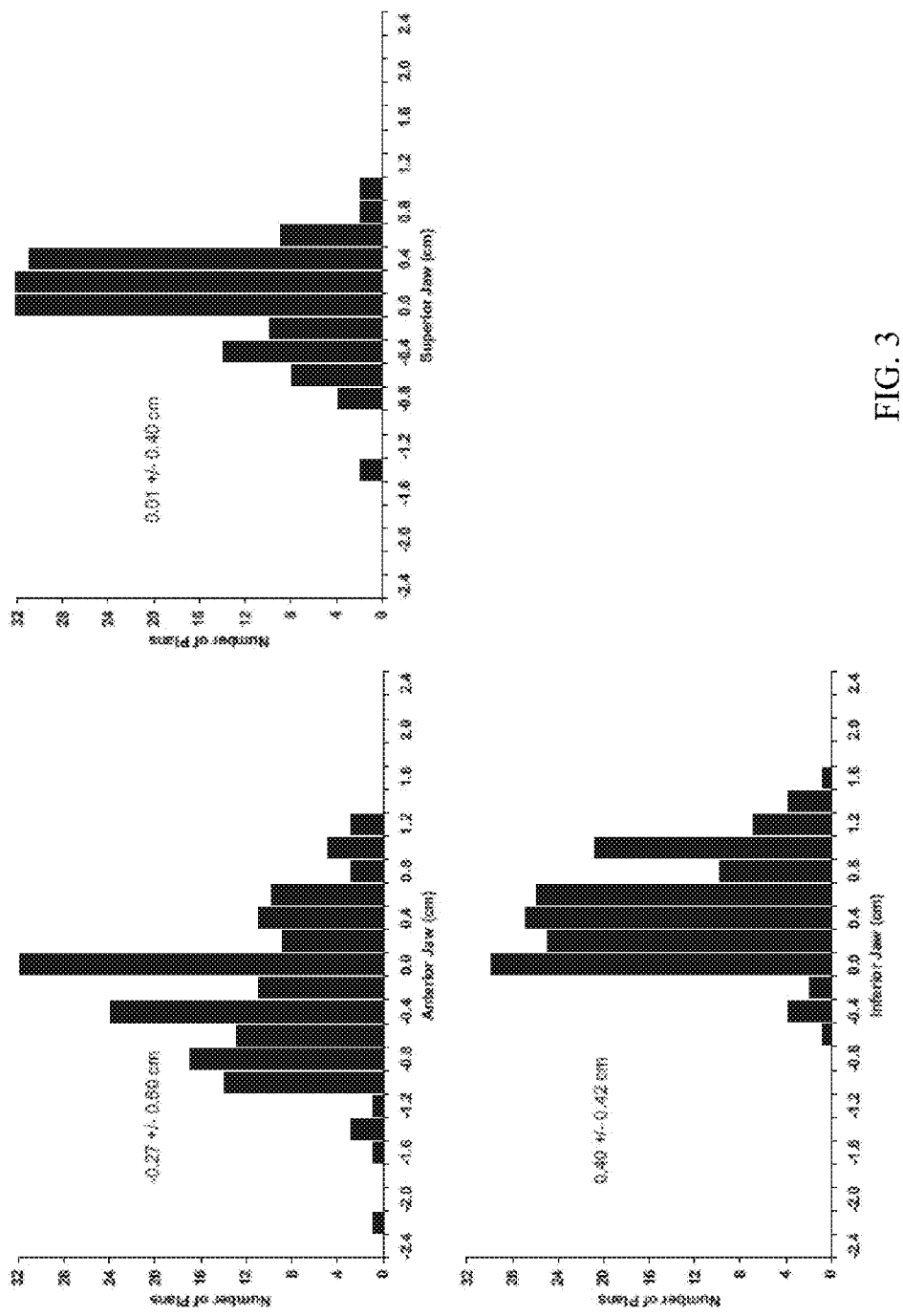

Beam parameters for the automatically generated plans were scored against the parameters from the conventional clinical plans. FIGS. 2-4 show example distributions of the differences between the two plans for gantry and collimator angles (FIG. 2), jaw positions (FIG. 3) and beam isocenter location (FIG. 4).

FIG. 2 shows the distribution of differences between the automatically generated plans and the clinical plans, for the gantry angle (left chart) and for the collimator angle (right chart), from this example study. The differences between the automatically generated plans and the conventionally generated plans for the gantry (in this study, $-0.13+/-1.54$, $p=0.303$) and the collimator (in this study, $0.08+/-2.91$, $p=0.311$) were found to be not significantly different according to the paired t-test.

FIG. 3 shows distributions of differences between automatically generated and manually generated plans for position of the anterior (top left chart), superior (top right chart) and inferior jaws (bottom left chart), from this example study. The posterior jaw position was defined to be zero and the anterior jaw setting included skin flash. The automatic treatment planning method was found to add 2.0 cm of skin flash for the anterior jaw. The differences for the anterior jaw (in this study, $-0.27+/-0.60$ cm, $p<0.001$) and the inferior jaw (in this study, $0.40+/-0.42$ cm, $p<0.001$) were found to be significantly different while the differences for the superior jaw (in this study, $-0.01+/-0.39$ cm, $p=0.873$) were found to be not statistically different according to the paired t-test.

FIG. 4 shows distributions of differences between the automatically generated and manually generated plans for beam isocenter position in lateral (left chart) and anterior-posterior directions (right chart), from the example study. The superior-inferior isocenter coordinate was set according to the markers placed at CT simulation and therefore was found to be the same for both the automatically generated and conventionally generated plans. The differences for the lateral isocenter coordinate (in this study, $0.21+/-0.06$, $p=0.17$) and the anterior-posterior isocenter coordinate (in this study, $0.19+/0.38$, $p=0.06$) were found to be not significantly different according to the paired t-test.

In this example study, the results show agreement between the beams generated using the automated treatment planning method and beams generated by the conventional manual method. Some discrepancies may be seen for the anterior jaw position (the jaw which defines the skin flash that accommodates breathing) and the inferior jaw position. This may be because, in the example automated treatment planning method used in this study, empirical rules based on the marker location were used to set these values. In this example, the anterior jaw position was defined as 2.0 cm from the patient surface, although other positions may be used. Therefore, the amount of skin flash may be invariant between patients. Similarly, the inferior jaw position was consistently defined by the inferior marker. In other examples, the automated treatment planning may vary how the collimator jaw positions are determined.

For comparison, plan parameters were also scored for both the automatically generated and conventionally generated plans (examples are shown in Table 3 of FIG. 15. It was found that automatically generated and conventionally generated plans were relatively equivalent in terms of monitor units (MU) for all dose-fractions. It was also found that the automatically generated plans may require one more segment than the conventionally generated plans. This may be because the automatically generated plans included the cavity in optimization calculations, whereas manually generated plans may not. This may be due to the specific calculations used in the automated treatment planning method (e.g., the specific empirical values in the lookup tables), and may be varied as suitable. Based on this comparison, it may be expected that little or no additional time will be required to deliver the automatically generated plans on the treatment units, compared to conventionally generated plans. In some examples, treatment time may be reduced for delivering the automatically generated plans, compared to conventionally generated plans.

The optimized breast target volumes generated by the automated and clinical plans were also scored for agreement. FIG. 5 shows distributions of volume overlap (left chart) and Hausdorff distances (right chart) between the automatically calculated breast volume and the conventionally determined breast volume, from the example study. The target volume overlap is the ratio of the intersection to the union of the two volumes and the Hausdorff distance is defined as the maximum distance of the distribution of the closest distances at each point in one volume to every point in the other volume. The actual target volumes for the automated plans and clinical plans were found to be statistically different ($p<0.001$) according to the paired t-test.

The mean target volumes of the automatically generated plans (in this study, $692.7+/-406.2$ cc) were found to be larger than the clinically derived target volumes (in this study, $663.6+/-387.2$ cc) by <5%. The mean fractional volume overlap between the two target volumes was, in this study, $0.85+/-0.05$ and the mean Hausdorff distance measuring the largest distance discrepancy between the two volumes expressed as a vector was, in this study, $1.21+/-0.49$ cm. These differences were not found to affect clinical outcomes. Even though the target volumes were larger in the automatically generated plans (i.e., the automatically generated plans had larger treatment fields), the treatment coverage in both cases was the same. Further, these differences also did not impact irradiation of critical structures (e.g., the hearts and lungs). That is, the automatically generated treatment plans did not deliver more dosage to critical structures than manually generated plans because of these differences. These differences may arise due to the clinical requirement specified in the automated method to always ensure that the cavity was covered by a 1.0 cm margin, while the manually generated plans did not always achieve this criterion. Because the automatically generated plans always aimed to cover the cavity by at least this margin, the result was gantry angles and isocenter placement which ultimately exposed more breast tissue and hence increased the target volume.

Figure 6:
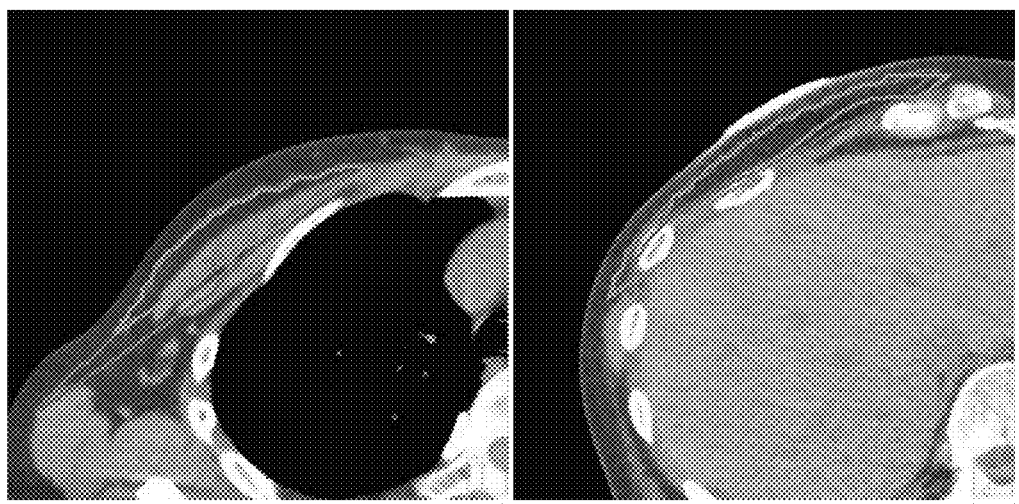
FIG. 6 shows example CT images treatment volumes generated using an example automated method and a conventional method.

The greatest mismatch was seen in areas of non-breast tissue, in which the breast volume was extended due to changes in patient shape posteriorly, which is shown in FIG. 6. FIG. 6 shows example CT images comparing treatment volumes generated using the example automated treatment planning and using conventional treatment planning, for the patient with the largest Hausdorff distance in the study for superior (left image) and inferior (right image) aspects of target volume. In this example, the fractional volume overlap was found to be 0.82 and the Hausdorff distance was found to be 3.17 cm. The largest discrepancy in the volumes was found to be posterior to the actual breast tissue, which may be resulting from the large lateral change in the patient's surface contour.

Although there may be discrepancies between the target volumes generated for the automatically generated and conventionally generated plans, the plans were found to be dosimetrically equivalent. A comparison of example plans is shown in Table 4 of FIG. 16. Clinically the $D_{99\%}$ was evaluated for minimum target coverage (e.g., limit >0.92 of prescription dose) and the $D_{2cc}$ was evaluated for maximum dose (e.g., limit <1.08 of prescription dose). The automatically generated plans were found to have lower maximum doses within the target volume, however the maximum dose limit may be exceeded in some of the automated plans as well as some of the clinically delivered plans. The larger target volumes automatically delineated in the automatically generated plans was not found to translate into increased heart or ipsilateral lung doses, compared to conventionally generated plans.

Figure 7:
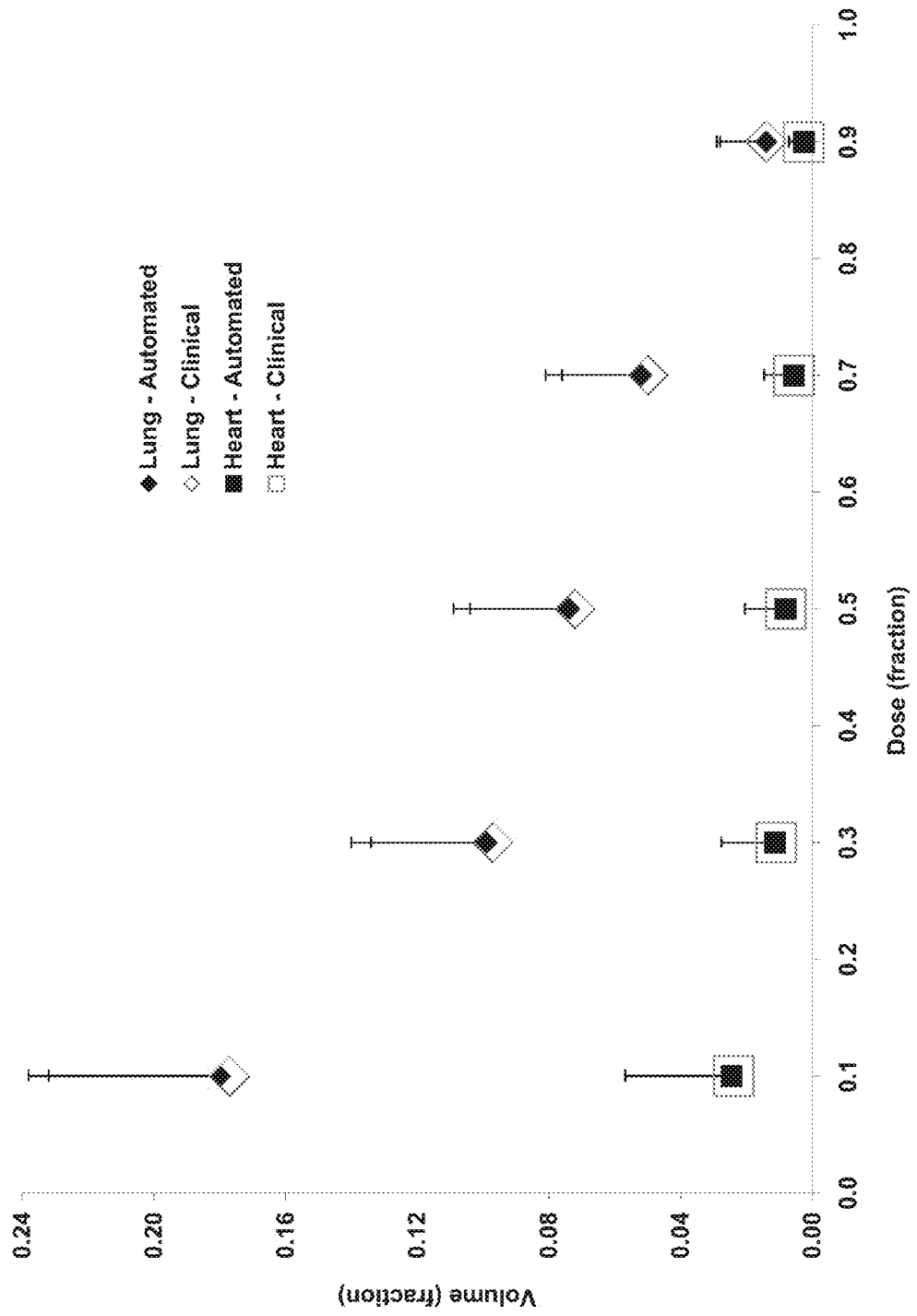
FIG. 7 shows an example dose-volume histogram comparing an example automated method and a conventional method.

FIG. 7 shows a comparison of example dose as the fractional of the prescription dose. In this comparison, points are mean values with error bars showing one standard deviation. The dose-volume values were not found to be statistically different according to the paired t-test for any point. There were no significant differences found between the automated and conventional plan ipsi-lateral lung doses at any dose point measured and for the individual left and right ipsilateral lung doses at any dose point measured. The fractional ipsi-lateral lung volume at 20 Gy (V20) was also found to be not significantly different between the automated and clinical plans (in this example, 0.077+/−0.036 vs. 0.075+/−0.033, p=0.54), however the V20 for left-sided patients was found to be higher for the automated plans (in this example, 0.082+/−0.040 vs. 0.076+/−0.034, p=0.03). The mean heart dose between the automated and clinical plans (in this example, 108.2+/−90.5 cGy vs. 106.1+/−89.6 cGy, p=0.27) was also found to be not different.

Comparison of the clinical acceptability of the treatment plans generated using the example automated treatment planning method and system and the conventionally generated treatment plans was performed in a randomized double-blinded study by an experienced breast radiation oncologist. Example results of this comparison are shown in Table 5 of FIG. 17. In the majority of cases (in this example, 125 of 158, 79.1%) the two plans were deemed clinically equivalent with respect to all the evaluated parameters. Automated plans (in this example, 13 of 158, 8.2%) and conventional plans (in this example, 20 of 158, 12.7%) were deemed clinically favorable over the alternative plan. In this example study, conventionally generated plans were found to have more homogenous dose distributions, but may suffer from higher maximum doses. In the eight automated plans deemed more favorable for the maximum plan dose, four plans were found to be improved compared with the conventional plans. As a result two conventional plans were rejected for clinical acceptability by the radiation oncologist.

As an example benchmark, the time between the last user interaction and a completed treatment plan was recorded. The entire automated treatment planning process for generating all target volumes, normal tissue volume and optimization volumes, in addition to the beam parameter optimization, IMRT optimization and final dose calculation was, in this study, found to be less than seven minutes (in this example, 6:50+/−1:08 minutes). This speed is expected to be replicable on any conventional treatment systems.

Applications and Variations

The automated treatment planning method and system of this example study may provide a relatively fast and efficient manner for generating treatment plans, for example for treatment of the breast, with clinical results that may be comparable to or better than conventional manually generated treatment plans. The automated treatment planning methods and system may be implemented on conventional treatment systems, and may use common anatomical landmarks (e.g., from CT simulation) as inputs, to allow for relatively straightforward integration into clinical practice. The disclosed automated treatment planning systems and methods may automate some or all of the conventional manual treatment planning steps and decisions conventionally performed by the radiation therapy planner.

Use of the disclosed automated treatment planning methods and systems may help improve patient access to high-quality IMRT treatments by speeding up and/or simplifying the planning process and may also help to reduce the cost of adopting a fully inverse planned IMRT treatment, for example for two-field tangent breast treatment.

In addition, the disclosed automated treatment planning methods and system may provide for automated treatment planning that require reduced or minimal user interaction (e.g., only require interaction at the beginning of the planning process), which may allow the user to initiate generation of multiple plans (e.g., for different patients) in parallel, which may further improve efficiency and/or patient access.

The automated treatment planning method and system may also be configured to prevent the beam from passing through the contra-lateral breast. This may be achieved by preventing the medial part of the beam from being moved away from the medial markers toward the contralateral breast. The user may also specify the clinical requirement for the lateral part of the beam to only move posteriorly. This may result in forcing only gantry optimization for the posterior direction and not allow the beam to be placed in a shallow position with the lateral part of the beam moving anteriorly.

In other examples, this limitation may not be present, which may be useful, for example, where irradiation of the contra-lateral breast may be required to achieve coverage of the target volume. In some examples, the automated treatment planning method and system may generate plans based on a single beam energy. However, in other examples, the automated treatment planning method and system may be configured to generated plans based on one or more beam energies (i.e., mixed beam energy).

The automated treatment planning method and system may employ a direct aperture optimization method in the clinical planning system, such as one that has been reported previously for breast IMRT (11)(13)(14). In some studies, the direct aperture optimization has been shown to be superior to 3D conformal and other IMRT methodologies for breast radiation therapy (11)(13). In addition, the direct aperture optimization may be relatively efficient and may produce relatively robust dose distributions, which may be useful in an automated treatment planning process. In some examples, an advantage of the direct aperture optimization approach may be that there may be no final conversion from an idealized fluence to multileaf collimator (MLC)-defined segments. In this approach, a conversion may be required at an intermediate step in the optimization. At this point, depending on the complexity of the fluence, the optimization may fail to convert the fluence to deliverable segments. For conventional manual planning, a solution may be to decrease the minimum segment area to allow the optimization to continue. In examples of the automated treatment planning method and system, in which there is no user interaction, a solution may be to adjust the lookup table (e.g., as shown in Table 1) for the maximum number of segments and the minimum segment area to make the automated process relatively more robust to the conversion errors that may be seen during conventional planning.

In place of or in addition to the lookup tables described herein, empirical rules/relationships may also be embodied and defined using other suitable methods, including statistical models, machine learning or neural nets, for example. Such methods may be based on a large number of previous treatment plans and outcomes, and may further exhibit self-learning or adaptation to refine the empirical rules/relationships as additional data becomes available.

User Interface

In some aspects, the present disclosure provides a user interface suitable for carrying out examples of the disclosed automated treatment planning methods. Although described with reference to treatment of breast tissue, it should be understood that the user interface may be modified for use with treatment planning for other tissues. For example, the automated method may be used for treatment planning for any treatment site that has a standardized treatment planning approach. The clinical requirements, optimization parameters and/or technical parameters may be different, however the concept of the automation based on input that are clinical requirements or answers to clinical questions would still be applicable.

As an example, for treatment of the prostate, if the overlap between the target volume and the rectum was a specified clinical requirement, then the automated method may use an empirical rule to determine that the number of beam segments to use should increase by 5 from the nominal number of segments. For treatment of breast tissue, there are typically more clinical requirements than for treatment of most other sites, since the beam geometry typically used is constrained, and generic IMRT optimization approaches may not be suitable for producing treatment plans which meet the technical requirements for tangential breast treatment planning, without further manual modifications. Thus, for applications in treatment of other tissues, some of the requirements and considerations described for treatment of the breast may not be used.

The user interface may be provided as part of an example automated treatment planning method, for example displayed on the screen of an example automated treatment planning system.

The user interface may be designed to present the user with one or more selectable clinical options for automatically generating a radiation therapy treatment plan. This may differ from conventional treatment planning in which the user interacts with the treatment planning system by specifying technical parameters and/or optimization parameters directly, rather than clinical requirements. Conventionally, these technical parameters may be used by the planning system to generate a plan, although there may be limitations in what the conventional treatment planning system can use an input. Typically, the conventional treatment planning system may rely on dose-volume objectives used to direct an optimization engine.

In contrast, the disclosed interface may allow the user to specify clinical requirements directly, which may be then used to generate suitable technical parameters automatically. In some examples, the interface may also provide the user with an option to specify more parameters than dose-volume objectives, for example where the user may wish to force treatment plans to have certain characteristics.

The disclosed interface may help to facilitate complete automation of treatment planning, since once the clinical criteria are set, control may be turned over to the automated treatment planning method to set all the necessary parameters in the treatment planning to achieve the clinical requirements set by the users. For example, the disclosed interface may provide an option to specify different modes for treatment to set a number of clinical parameters at once which may correspond to achieving the same clinical objective. In some examples, the disclosed interface may provide an option to select different algorithms for achieving a particular clinical objective.

The disclosed interface may provide one or more default settings for the clinical requirements, for example predetermined settings that may apply to the majority of patient, however the user may additionally be provided with different algorithms and/or options that may enable the user to select for generation of treatment plans where there may be clinical motivation to deviate from the routine case.

The ability to specify clinical requirements rather than technical requirements and/or optimization parameters may be more intuitive and also may make the process independent of the specific treatment planning system used, as the clinical requirements may be independent of the specific system technology. By allowing the user to input clinical criteria to generate a treatment plan rather than technical parameters, examples of the disclosed interface may allow a user with no technical experience to generate treatment plans. As well, examples of the disclosed interface may allow a user to generate treatment plans directly by simply specifying their clinical intent. Without any knowledge of how to actually generate a plan (e.g., the specific technical parameters involved) or the details about using treatment planning software or system, a user may provide clinical requirements as input, using an example of the disclosed interface, and have a treatment plan generated automatically using an example of the disclosed automated treatment planning methods and systems.

Example of Treatment Planning User Interface

An example of the user interface is now described with reference to automated treatment planning for breast tissue. However, it should be understood that the user interface is not limited to treatment of the breast and may be used (e.g., with the appropriate modifications) for other therapy planning. The user interface may be suitable for use in the automated methods and systems for treatment planning described above.

In examples where the user interface and the automated methods and systems are used for planning radiation therapy for breast tissue, clinical requirements may include, for example, patient separation, amount of area/volume of lung in the treatment field, amount of whole breast volume in the treatment field, delineated cavity volume in the treatment field (with a geometric margin), whether the treatment beam should include the wire outlining the breast volume (with a geometric margin), and the amount of shielding for non-target tissues.

Such example clinical requirements, as well as those discussed elsewhere in the present disclosure, may be used to automatically determine appropriate technical parameters for the treatment plan.

For example, the disclosed method may accept as input a clinical requirement to fix the medial and/or lateral beam adjustment onto the medial and/or lateral markers (as defined during setup using CT simulation, for example). The default selection (i.e., if no user selection is made) may be to allow automated adjustment of both the medial and lateral portions of the beams for placement. The user may be provided the option to fix the medial and/or lateral adjustment points. When one or both of the medial and lateral adjustments are fixed to a user-defined point, the automated calculations will be constrained to produce a treatment plan in which the gantry angle causes the beam to fall on the medial and/or lateral markers, as specified.

The disclosed method may accept as input a clinical requirement to force the lateral portion of the treatment beam to fall anterior or posterior of the lateral marker. The default selection may be to allow automated positioning of the lateral part of the beam. When the user provides input that the lateral part of the beam should be placed anterior or posterior of the lateral marker, the automated calculations will be constrained to produce a treatment plan in which the gantry angle causes the beam to fall anterior or posterior of the lateral marker, as specified.

Another clinical requirement that may be accepted as input is a user selection specifying the average amount of lung volume that may be covered by the treatment field. This may be specified qualitatively by the user (e.g., a selection of "more lung" or "less lung"), in which case pre-defined lung volumes may be used (e.g., 0.0 cm lung volume where "less lung" is specified, or 4.0 cm lung volume where "more lung" is specified). This may alternatively be specified quantitatively by the user, for example as an average lung distance in cm. When the lung volume is inputted as a clinical requirement, the automated calculations will be constrained to produce a treatment plan in which the gantry angle causes the beam to achieve the desired amount of lung coverage. An empirical table, such as Table 2, may be used by the automated calculations to calculate the suitable gantry angle to achieve this constraint.

The user may also request breast size correction as a clinical requirement. This input may instruct the automated calculations to calculate and take into account the size of the patient's breast (e.g., as determined by breast separation and breast height values) when determining the appropriate amount of lung volume and thus the appropriate gantry angle for the beam. For example, when the user selects this input, the breast size of the patient may be automatically calculated in order to determine the suitable empirical lookup curve (e.g., selected from Table 2) to use in calculating the suitable gantry angle. For example, the lookup curve to be used when a small breast size has been determined may result in beam placement that covers less of the lung volume, as compared to beam placement where a nominal breast size is determined.

Another example clinical requirement that may be inputted by the user and factored into the disclosed automated treatment planning is a specification of the maximum lung distance allowed in the treatment field. This specification may be used in place of or in addition to specification of the lung volume, as described above. Again, the automated calculations may use an empirical lookup table, such as Table 2. Since the maximum lung distance is specified in this instance, rather than the average lung distance, the automated calculations will be constrained to produce a treatment plan in which at least the specified lung distance is covered by the treatment beam.

Another clinical requirement that may be inputted by the user may be specification of a geometric distance for post-surgical cavity optimization. The default value for this cavity optimization distance may be 1.0 cm (this value may be preset based on the most commonly used value, for example). When this specification is received as input, the automated calculations will be constrained to calculate a gantry angle that places the treatment beam such that the specified cavity margin is achieved.

A specification of medial proximity correction may be a clinical requirement inputted by the user. When this specification is received as input, the automated calculations will be constrained to produce a treatment plan to provide as much medial coverage as possible for cavities that are located medially. This specification may be on by default.

The user may also select options that, while not necessarily conventionally considered clinical requirements, may constrain the automated calculations. For example, the user may directly specify a desired value or range of values for the collimator angle, to directly influence the automated collimator optimization calculations. For example, the user may require the collimator angle to be larger (e.g., "rotate more") or smaller (e.g., "rotate less") than a nominal amount. This option may also be selected when the user is not satisfied with the first treatment plan generated and wishes to re-calculate the treatment plan to achieve a different collimator angle. Typically, by rotating more, more shielding is achieved for tissues inferior of the diaphragm and a larger margin is provided for treating cavities located superiorly. Conversely, by rotating less, typically more shielding is provided for lung tissues superiorly and a larger margin is provided for treating cavities located inferiorly. Another option allowing the user to apply a constraint may be an option to specify that coverage of the wire area overrides the collimator optimization calculations. Selection of this option constrains the automated calculations such that the collimator angles are calculated to ensure the entire wire area is covered in the treatment plan, overriding any conflicting collimator optimization calculations.

Wire optimization options may be inputted by the user as clinical requirements. For example, the user may specify that the wire may be outside the treatment field or entirely inside the treatment field, and the user may also be provided the option to specify the amount by which the wire is inside or outside the treatment field. This specification constrains the automated calculations to calculate beam parameters to cause the beam coverage to include or exclude the wire, and by the specified amount. This may be specified separately for lateral and medial portions of the beam. Automated wire optimization calculations may be performed based on automatic segmentation of the wire from the image dataset.

Similarly, the user may input as a clinical requirement the specification that coverage of the wire area takes priority over shielding of non-target tissues. By default, the treatment plan may be automatically calculated such shielding of non-target tissues takes priority over coverage of the wire area (this may be typically the case, such as where dosage to non-target tissues such as the lung and heart should be minimized). When the user inputs the requirement that coverage of the wire area takes priority, the automated calculations will be constrained to ensure that the calculated beam parameters cover the entire wire area, even when non-target tissues would be irradiated. This may also be specified numerically as a margin by which coverage of non-target tissues is permitted. For example, the user may specify that coverage of the wire area should take priority provided irradiation of non-target tissues does not exceed a margin of 1.0 cm.

Another clinical requirement based on coverage of wire area is the option for the user to specify that optimization for coverage of the wire area takes priority over other optimization calculations for the gantry angle. Selection of this clinical requirement constrains the automated calculations to optimize beam parameters such that the beam covers the entire wire area, even if this conflicts with optimization of the gantry angle (e.g., according to specified medial and lateral adjustments, as described above). This may not be the default setting, as typically it is not desirable to optimize for wire area coverage over all else.

The user may also specify, as a clinical requirement, the amount of shielding for non-target tissues (e.g., the heart, tissues inferior of the diaphragm, and the humerus). This may be specified as a maximum margin of non-target tissues that may be included in the treatment field. For example, the user may specify that up to 1.0 cm of a non-target tissue, such as the heart, may be included in the treatment field of the primary segment. Alternatively, this may be specified as the minimum margin of shielding for non-target tissues. For example, the user may specify that at least 5.0 cm of a non-target tissue be kept out of the treatment field.

The automated calculations may take into account additional empirical relationships that may not be based on directly inputted clinical requirements.

The separation on each treatment slice may be measured for a particular gantry, collimator angle and isocenter position. If the separation value is determined to be greater than a predefined threshold value (e.g., 20-30 cm), the automated calculations will be constrained to produce a mixed energy treatment plan using a primary beam at nominal energy together with higher energy beams that are modulated beam segments.

Automated gantry optimization in an example of the automated method involves the use of appropriate empirical lookup curves and constraints based on the user's inputted clinical requirements. Based on the inputted requirements, a lookup curve is selected and a target coverage amount is determined empirically from the lookup curve. The beam parameters are then optimized (e.g., by iteratively calculating different beam configurations until the target coverage amount is achieved). Cavity optimization may take priority over gantry angle optimization. Cavity optimization may involve satisfying a specified margin from the edge of the treatment beam to the post-surgical cavity. If the optimized gantry angle, based on the empirical lookup values, does not satisfy the specified cavity constraints, then the gantry angle is further adjusted to achieve the cavity constraint at the cost of gantry angle optimization.

To accommodate a user-specified shielding margin, an initial beam may be automatically calculated based on optimization of the gantry angle, the beam isocenter position and the collimator angle, without consideration of shielding. The size of the beam may be set based on consideration of the target treatment area, and may be initially rectangular in shape. User-specified shielding is then taken into account and the beam parameters are recalculated to remove the shielded areas from the treatment field. The resulting beam may be used as the primary segment for the treatment plan produced, with additional segments being created through further optimization steps, for example.

FIG. 9 shows an example of a user interface suitable for example automated radiation therapy treatment planning methods and systems, in this example for treatment of breast tissue. This example interface may provide for selection of a set of predefined or default settings for the clinical requirements.

In the example of FIG. 9, the user interface may provide one or more options for selecting the setup used (in this example, the CT simulator and CT machine may be selected), and one or more options for selecting the treatment (in this example, the prescription may be selected).

In the example of FIG. 9, the user interface may also provide an option for selecting the treatment site. For example, under "Site", selecting either the "Whole Breast" or "Chestwall" option may enable a specific set of predefined or default settings that are site specific. For example, selecting the "Chestwall" option may disable "High Energy" beams, may disable "Cavity Overrides Gantry Optimization" and/or may enable "Wire Overrides Gantry Optimization". These and other settings may be described below with reference to an example user interface for customized settings.

In the example of FIG. 9, the user interface may also provide an option for selecting the treatment mode. For example, under "Mode", selecting either the "Breast Coverage" or "Lung Sparing" option may enable a specific set of predefined or default settings based on the treatment intent. For example, selecting the "Whole Breast" option may indicate that the user desires the treatment plan to be generated to ensure that the whole breast volume is be in the treatment beams. For example, the "Lung Sparing" option may be selected to indicate that the user desires the treatment plan to be generated such that the whole breast coverage may be compromised (if necessary) in order to reduce the lung volume. In some examples, the Cavity (described further below) may still be covered by the specified margin in the "Lung Sparing" mode unless explicitly de-selected, for example using customized settings.

The example user interface of FIG. 9 may also provide an option to access "Advanced Settings", which may provide detailed options for user selection, for example where the user wishes to customize settings (e.g., certain clinical requirements) for a treatment plan.

The "Site" and "Mode" options provided by the example user interface of FIG. 9 may provide a relatively quick way for the user to change several advanced settings with a single selection. Such advanced settings may be further modified/customized, for example using the example user interface of FIG. 10.

Figure 10:
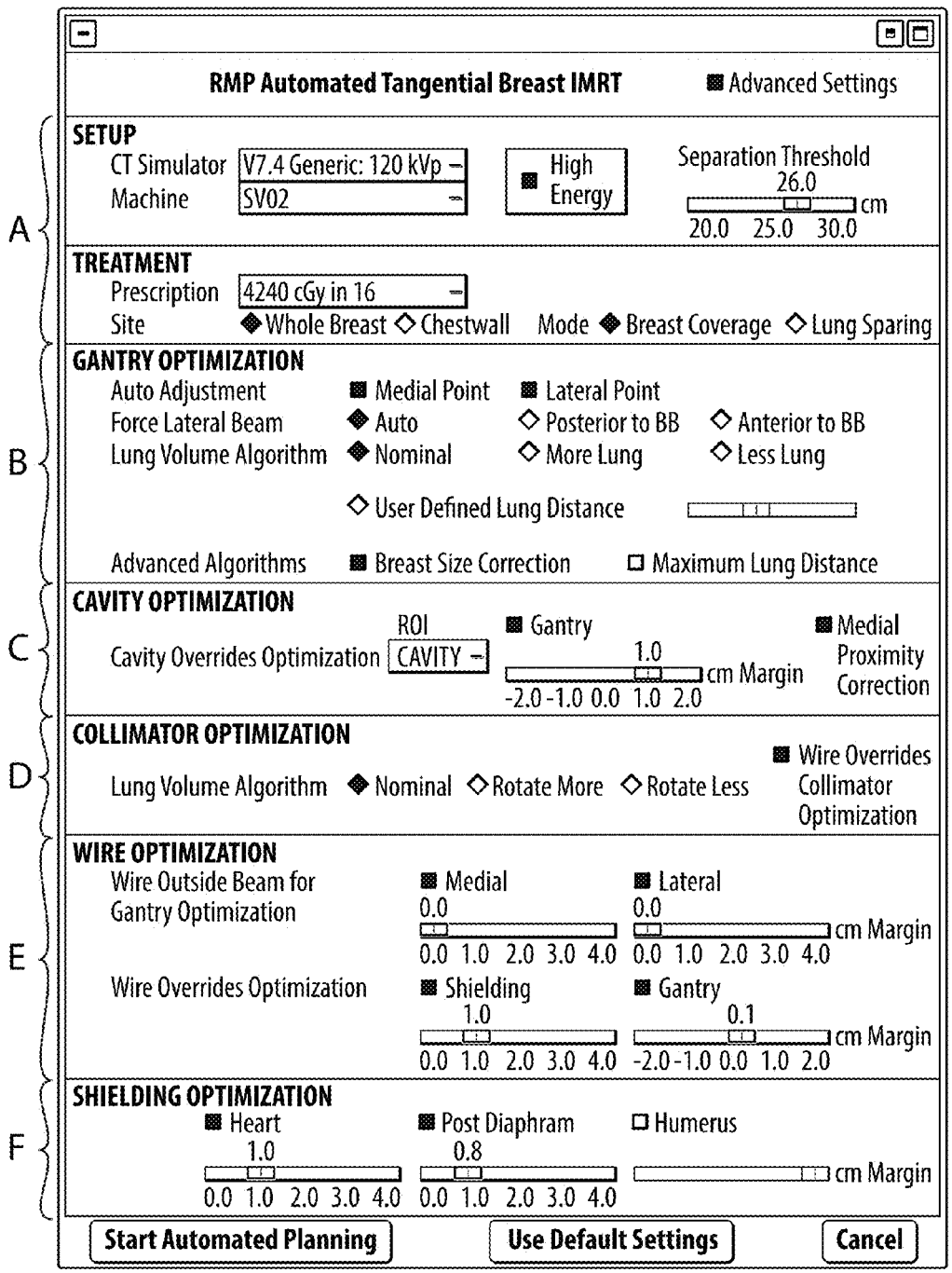
FIG. 10 shows another example user interface suitable for an example method of automated radiation therapy treatment planning.

FIG. 10 shows an example of a user interface suitable for example automated radiation therapy treatment planning methods and systems, in this example for treatment of breast tissue. This example interface may provide for selection of detailed advanced or customized settings.

In the example of FIG. 10, the user interface may expand or extend from the example user interface of FIG. 9. For example, the example user interface of FIG. 10 may include, in a first portion (A) "Setup" and "Treatment" options similar to the example of FIG. 9. In the example of FIG. 10, the first portion (A) may further provide a "High Energy" option and a "Separation Threshold" option. Under "Separation Threshold", the user may be provided with an option to specify a separation value (in this example, ranging from about 20.0 to 30.0 cm) for each slice. If the separation threshold on ANY slice is exceeded, the automated treatment planning method may generate a treatment plan that may use high energy for the direct machine parameter optimization (DMPO) generated segments, while the first segment (open segment) may still use the nominal energy. To force high energy segments, the user may specify a low separation threshold (e.g., 20.0 cm). In this example, the first segment of each beam may still be at the nominal energy. In some examples, where the radiation treatment system may deliver only one energy, the automated treatment planning calculations may result in a treatment plan that uses the nominal energy for both the open beam and the segments, regardless of whether the "High Energy" option is selected.

In the example of FIG. 10, the user interface may also include a second portion (B) for "Gantry Optimization". Options provided under "Gantry Optimization" may be used to determine the gantry angle of the treatment beam. For example, in preset or default settings, the automated treatment planning may determine the gantry angle based on an automatically determined volume of lung based on the Medial and Lateral anatomical markers. Further options for determining the gantry angle may be provided by options under "Cavity" and "Wire", for example, as discussed further below.

"Gantry Optimization" may provide an "Auto Adjustment" option. The "Auto Adjustment" option may allow the user to specify whether the Medial Point and/or Lateral Point, which may define the medial and lateral aspects of the beam, respectively, are adjusted by the automated treatment planning calculations or whether the points are fixed. For example, if the user's intent is to ensure the medial aspect of the breast is covered in the treatment beam, the user may indicate that the automated treatment planning calculations should cause the treatment beam to pass through the initial Medial Point (i.e. the Medial breast bone), for example by de-selecting the "Auto Adjustment" of the "Medial Point" option.

"Gantry Optimization" may also provide a "Force Lateral Beam" option. The "Force Lateral Beam" option may allow the user to specify the gantry optimization of the lateral aspect of beam relative to Lateral point. In this example, the "Auto" option may be selected to cause automatic determination of the direction based on the lung volume encompassed by the tangential beams that passes through the Medial and Lateral points. In this example, the "Posterior to BB" or "Anterior to BB" (where "BB" stands for the ball bearing marker) options may be selected by the user to indicate that the automated treatment planning calculations should position the lateral part of the beam either posterior or anterior, respectively, when the desired direction of the lateral beam is opposite to the direction that would normally be determined based on the lung volume. For example, if there is very little lung in the field with the beams initially passing through the Medial and Lateral points, and the user's intent is to minimize the amount of lung further, in "Auto" mode, the automated treatment planning calculations would attempt to increase the lung in the field by moving the Lateral point posterior to the BB. However, the user can select the "Anterior to BB" option to ensure the results of the calculations do not increase the lung in the field and force the gantry optimization to only place the lateral aspect of the beam anterior to the Lateral point.

Under "Gantry Optimization", there may be a "Lung Volume Algorithm" option. This option may allow the user to set the target lung volume that the automated treatment planning calculations should aim to achieve. Selection of this option may not affect the lateral beam direction relative to the BB as discussed above, but rather the "Lung Volume Algorithm" option may change the target volume value. For example, the "Nominal" option may be suitable in the majority or cases and selection of this option may result in calculations that include a lung volume consistent with clinically acceptable values. In this example, selection of the "More Lung" option may result in calculations that may set the target lung volume to a higher value (i.e. allow more lung in the treatment beam), while selection of the "Less Lung" option may set the target lung volume to a lower value (i.e. allow less lung in beam).

Under "Gantry Optimization", there may an option for "User Defined Lung Distance". This option may provide the user an option to enter a specific target lung distance. The user may specify the target lung volume based on the 1) maximum lung distance by also selecting the "Maximum Lung Distance" option in the "Advanced Algorithms" section or 2) mean lung distance by de-selecting the "Maximum Lung Distance" option. For example, if a patient has had previous treatment and the user's intent for the current treatment is to spare more lung than is typically accepted, the user may select the "Less Lung" option. In another example, if a patient with poor lung function cannot have more than 0.5 cm of lung in the beam, the user may select the "User Defined Lung Distance" option with a value of 0.5 cm and also may select the "Maximum Lung Distance" option under "Advanced Algorithm".

The "Advanced Algorithms" option may provide "Breast Size Correction" and "Maximum Lung Distance" options. The "Breast Size Correction" option may be selected to change the target Breast volume value for the automated treatment planning calculations. This option may include both a small volume and large volume correction. The "Maximum Lung Distance" option may be selected to cause the automated treatment planning calculations to take into consideration both the volume of lung in the field and the maximum lung distance for gantry optimization. For example, the selection of the "Maximum Lung Distance" option may result in decreased lung in the treatment field.

In the example of FIG. 10, the user interface may also include a third portion (C) for "Cavity Optimization". Options provided under "Cavity Optimization" may be used to further optimize calculation of the gantry angle.

Options under "Cavity Overrides Optimization" may be selected to specify that the minimum distance between the Cavity ROI specified and the beam edge should be calculated to be greater than the Cavity Margin selected (which may be, for example, in the range of about −2.0 to about 2.0 cm). Selection of a negative margin may indicate that the calculated beam may go inside the Cavity ROI by the margin specified. In some examples, Cavity delineation may be optional for the automated treatment planning. In such examples, it may not be necessary to de-select the "Cavity Overrides Gantry Optimization" option where the Cavity is not delineated. In such examples, the automated treatment planning calculations may determine the number of contours in the Cavity ROI in order to determine the appropriate gantry optimization.

Under "Cavity Optimization", there may also be provided the option "Medial Proximity Correction". The automated treatment planning calculations may determine the location of the Cavity relative to the Medial and Lateral points. In some examples, for a Cavity located medially, selection of the "Medial Proximity Correction" option may cause the automated treatment planning calculations to calculate the medial aspect of the beam to be placed closer to the medial breast bone. In some examples, for a Cavity located laterally, the medial aspect of the beam, which may be determined from calculations for gantry optimization, may remain fixed, and only the lateral aspect of the beam may be corrected to achieve the specified margin to the Cavity.

In the example of FIG. 10, the user interface may also include a fourth portion (D) for "Collimator Optimization". Options provided under "Collimator Optimization" may be used to optimize calculation of the collimator angle. For example, the goal of the collimator optimization may be to reduce or minimize the amount of lung and normal tissue in the beam, for example by rotating the collimator angle.

Under "Lung Volume Algorithm", options may be provided, including, for example, "Nominal", "Rotate More" and "Rotate Less". The "Rotate More" or "Rotate Less" options may be selected when the user is not satisfied with the collimator angle determined by the "Nominal" setting. For example, selection of the "Rotate More" or "Rotate Less" options may cause the automated treatment planning calculations to apply different weighting factors to the distance of lung and normal tissue in the beam. This may result in calculations the may change the collimator angle between 0 and 5 degrees of the collimator angle calculation under "Nominal" settings.

Typically, these options would only be used when the standard or nominal collimator angle is not clinically justified. For example, if the user favors more or less collimator rotation from the start, this may be specified at the start. Alternatively, if the automatically generated plan does not provide the user with a desired collimator angle, the "Rotate More" or "Rotate Less" options may be selected and the automated plan calculations may be repeated.

Under "Collimator Optimization", a "Wire Overrides Collimator Optimization" option may be provided. The user may select this option to instruct the automated treatment planning calculations to determine a collimator angle that may still encompass the wire that is in the field following gantry optimization.

In the example of FIG. 10, the user interface may also include a fifth portion (E) for "Wire Optimization". Options provided under "Wire Optimization" may be used to add constraints to the optimization calculation of the gantry angle or to further optimize the gantry angle. For example, the automated treatment planning method may automatically extract the wire marker from the CT simulation image(s), and the delineated wire marker may be used for optimization calculations for the collimator angle, gantry angle, and/or shielding.

Under "Wire Optimization", options may be provided under "Wire Outside Beam for Gantry Optimization" for Medial and Lateral Beams. Using these options, the user may specify the desired gantry optimization relative to the wire defining the breast tissue. These options may be selected to define the limits or boundary conditions for gantry optimization.

For example, de-selecting the checkbox option (which may be the default setting for "Breast Coverage" mode) may result in automated treatment planning calculations that avoid gantry optimization that results in an isocenter point and gantry angle such that the beam is inside the wire (e.g., based on the isocenter slice).

For example, selecting the checkbox option (which may be the default setting for "Lung Sparing" mode) may result in automated treatment planning calculations that allow gantry optimization that results in the beam being inside the wire up to the margin specified by user (e.g., as indicated by a sliding bar, such as from the range of about 0.0 to about 4.0 cm). For example, the user-specified margin may be independent for the Medial and Lateral aspects of the beam. The user-specified margin may be used in automated treatment planning calculations as a maximum margin allowed and may not reflect the actual margin in the resultant calculated treatment plan. For example, for a patient with previous treatment to the contra-lateral breast, the user's intent may be to provide an extra margin anteriorly at the expense of covering the breast tissue, but avoid any compromised coverage of the breast laterally. In such an example, the user may select a margin of 4.0 cm for the Medial part of beam and a margin of 0.0 cm for Lateral part of beam, to cause automated calculation of an appropriate treatment plan.

Under "Wire Optimization", there may be options provided under "Wire Overrides Optimization—Shielding". For example, under default settings, automated treatment planning calculations may generate a treatment plan that excludes heart and non-breast tissue inferiorly (e.g., as set using shielding options, such as described further below). The user may select options to cause the automated treatment planning calculations to generate treatment plans in which the wire is not shielded. For example, the user may select the checkbox to cause the automated treatment planning calculations to reduce or eliminate shielding within the margin specified by the user (e.g., in the range of about 0.0 to about 4.0 cm), which may expose the wire in the first segment.

Under "Wire Optimization", there may also be options provided under "Wire Overrides Optimization—Gantry". For example, selection of this option may cause the automated treatment planning calculations to further optimize the gantry angle by following a minimum distance between the Wire and the beam edge that may be greater than the Wire Margin selected by the user (which may range, for example, from about 0.0 to about 4.0 cm). For example, selection of a negative margin may indicate that the calculated treatment plan may result in treatment beam placement inside the Wire by the margin specified.

In the example of FIG. 10, the user interface may also include a sixth portion (F) for "Shielding Optimization". Options provided under "Shielding Optimization" may be used to control the amount of shielding for non-target tissue to be provided in the calculated treatment plan. In some examples, the shielding specified by the user under this portion may be superseded by the shielding margin specified in the "Wire Overrides Shielding Optimization" portion described above. For example, the shielding margins under "Shielding Optimization" may be selected to specify the amount of non-target tissue (e.g., the heart, post-diaphragm tissues, humerus, etc.) that may be included in the calculated treatment field (e.g., in the range of about 0.0 to about 4.0 cm). For example, if the user's intent is to completely shield a particular non-target structure, the shielding margin may be selected to be 0.0 cm.

Although the user interface has been described with reference to automated treatment planning for treatment of breast tissue, it should be understood that the user interface may be varied (e.g., with appropriate options and setting ranges) to allow a user to specify clinical requirements for calculation treatment plans for other treatment areas.

For example, treatment of different tissues may have different clinical requirements (e.g., the treatment volume and the avoid volume may be different for different target tissues). In some examples, for treatment of different tissues, the technical parameters may be the same but may be adjusted according to different empirical rules.

Figure 18:
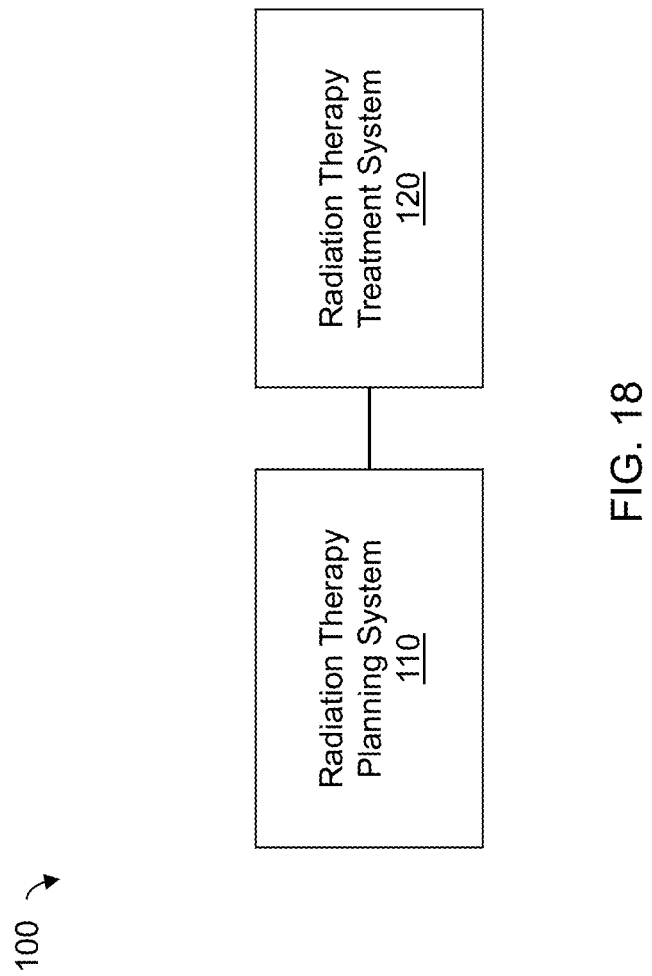
FIG. 18 illustrates a system comprising a radiation therapy planning system and a radiation therapy treatment system.

FIG. 18 illustrates a system 100 comprising radiation therapy planning system 110 as disclosed herein and radiation therapy treatment system 120.

The embodiments of the present disclosure described above are intended to be examples only. Alterations, modifications and variations to the disclosure may be made without departing from the intended scope of the present disclosure. In particular, selected features from one or more of the above-described embodiments may be combined to create alternative embodiments not explicitly described. It should be understood that although the disclosure describes a method and system, the disclosure also is directed to any non-transitory computer program products (e.g., CD, memory, disks) having code tangibly embedded therein for carrying out the described methods. The present disclosure is also directed to code, signals and other transitory media for carrying out the described methods. All values and sub-ranges within disclosed ranges are also disclosed. The subject matter described herein intends to cover and embrace all suitable changes in technology. All references mentioned are hereby incorporated by reference in their entirety.

REFERENCES

1. Kestin L L, Sharpe M B, Frazier R C, et al. Intensity modulation to improve dose uniformity with tangential 1. breast radiotherapy: initial clinical experience. Int J Radiat Oncol Biol Phys 2000; 48:1559-1568.
2. Vicini F A, Sharpe M, Kestin L, et al. Optimizing breast cancer treatment efficacy with intensity-modulated radiotherapy. Int J Radiat Oncol Biol Phys 2002; 54:1336-1344.
3. Harsolia A, Kestin L, Grills I, et al. Intensity-modulated radiotherapy results in significant decrease in clinical toxicities compared with conventional wedge-based breast radiotherapy. Int J Radiat Oncol Biol Phys 2007; 68:1375-1380.
4. Pignol J P, Olivotto I, Rakovitch E, et al. A multicenter randomized trial of breast intensity-modulated radiation therapy to reduce acute radiation dermatitis. J Clin Oncol 2008; 26:2085-2092.
5. Donovan E, Bleakley N, Denholm E, et al. Randomised trial of standard 2D radiotherapy (RT) versus intensity modulated radiotherapy (IMRT) in patients prescribed breast radiotherapy. Radiother Oncol 2007; 82:254-264.
6. Haffty B G, Buchholz T A, McCormick B. Should intensity-modulated radiation therapy be the standard of care in the conservatively managed breast cancer patient? J Clin Oncol 2008; 26:2072-2074.
7. Potters L, Steinberg M, Wallner P, et al. How one defines intensity-modulated radiation therapy. Int J Radiat Oncol Biol Phys 2003; 56:609-610.
8. Chen G P, Ahunbay E, Li X A. Automated computer optimization for 3D treatment planning of breast irradiation. Med Phys 2008; 35:2253-2258.
9. Whelan T, MacKenzie R, Julian J, et al. Randomized trial of breast irradiation schedules after lumpectomy for women with lymph node-negative breast cancer. J Natl Cancer Inst 2002; 94:1143-1150.
10. Shepard D M, Earl M A, Li X A, et al. Direct aperture optimization: a turnkey solution for step-and-shoot IMRT. Med Phys 2002; 29:1007-1018.
11. van Asselen B, Schwarz M, van Vliet-Vroegindeweij C, et al. Intensity-modulated radiotherapy of breast cancer using direct aperture optimization. Radiother Oncol 2006; 79:162-169.
12. Beauchemin M, Thomson K P B, Edwards G. On the Hausdorff distance used for the evaluation of segmentation results. Canadian Journal of Remote Sensing 1998; 24:3-8.
13. Ahunbay E E, Chen G P, Thatcher S, et al. Direct aperture optimization-based intensity-modulated radiotherapy for whole breast irradiation. Int J Radiat Oncol Biol Phys 2007; 67:1248-1258.
14. Zhang G, Jiang Z, Shepard D, et al. Direct aperture optimization of breast IMRT and the dosimetric impact of respiration motion. Phys Med Biol 2006; 51:N357-369.
15. McInerney T, Terzopoulos D. Deformable models in medical image analysis: a survey. Medical Image Analysis 1996; 1(2):91-108.
16. Pekar V, McNutt T R, Kaus M R. Automated model-based organ delineation for radiotherapy planning in prostatic region. Int J Radiat Oncol Biol Phys 2004; 60(3); 973-980; erratum 2005; 61(2); 635.

The invention claimed is:
1. A system comprising:
a radiation therapy treatment system; and
a planning system for automatically planning a radiation therapy treatment for delivery using the radiation therapy treatment system, the planning system comprising at least one processor coupled to at least one memory having computer-readable instructions encoded thereon, wherein the processor is configured to execute the instructions for:
determining at least one region of interest for the radiation therapy treatment;
using at least one clinical requirement to be met for the radiation therapy treatment where the at least one clinical requirement is relevant to the at least one region of interest, calculating at least one current technical parameter that controls a technical operation of the radiation therapy treatment system to satisfy the at least one clinical requirement using a predefined empirical relationship, the predefined empirical relationship comprising a previous technical parameter from a previously used radiation therapy treatment plan; and
generating a treatment plan comprising a set of technical parameters, including the at least one calculated current technical parameter, for the radiation therapy treatment for delivery using the radiation therapy treatment system;
wherein the radiation therapy treatment system delivers the radiation therapy treatment according to the generated treatment plan.
2. The system of claim 1, wherein the calculating of the at least one current technical parameter comprises using at least one optimization parameter determined from the predefined empirical relationship.
3. The system of claim 2 wherein the determined optimization parameter comprises an empirical value obtained from a lookup table.
4. The system of claim 3 wherein the lookup table contains empirical values determined from a plurality of previously used treatment plans.
5. The system of claim 2 wherein the optimization parameter is one of: a segment number, a segment area, a maximum lung distance value, and an average lung distance value.
6. The system of claim 1 wherein the at least one current technical parameter comprises at least one of: a gantry angle, a collimator angle, a collimator jaw setting, a treatment beam isocenter, and a treatment beam strength.
7. The system of claim 1 further comprising a display coupled to the processor for displaying a user interface, and an input device coupled to the processor for inputting a user-specified clinical requirement using the user interface.
8. The system of claim 7 wherein the user interface provides at least one default setting.
9. The system of claim 1 wherein the radiation therapy is for treatment of breast tissue.
10. The system of claim 1 wherein the at least one clinical requirement is one of:
specification of allowable non-target tissue in treatment field;
specification of margin of coverage of target tissue;
prioritization of coverage of target tissue;
prioritization of avoidance of non-target tissue; and
restriction of adjustments for one or more technical parameters in the set of technical parameters.
11. The system of claim 1 wherein the at least one region of interest is determined using an imaging modality selected from: magnetic resonance (MR), computer tomography (CT), cone-beam CT (CBCT), and positron emission tomography (PET).
12. The system of claim 1 wherein the determining of the at least one region of interest comprises identifying a position of at least one marker, and based at least partly on the identified marker position delineating a target volume for treatment, the region of interest comprising the delineated target volume.

13. The system of claim 12 wherein the calculating of the at least one current technical parameter is based at least partly on the identified position of the at least one marker.

14. The system of claim 1 wherein:
the determining of the at least one region of interest comprises identifying a position of at least one marker, and based at least partly on the identified marker position delineating a volume for treatment, the region of interest comprising the delineated volume; and
the processor is configured to execute the instructions for:
calculating a generated treatment field based at least partly on the calculated at least one current technical parameter;
identifying an avoid volume of the delineated volume within the calculated generated treatment field; and
repeatedly adjusting the at least one current technical parameter, and correspondingly re-calculating the generated treatment field and re-identifying the avoid volume based at least partly on the respectively adjusted at least one current technical parameter until the avoid volume is optimized at least partly in accordance with at least one optimization parameter determined from the empirical relationship.

15. The system of claim 14 wherein the at least one optimization parameter comprises minimization of the avoid volume.

16. The system of claim 14 wherein the avoid volume is optimized at least partly in accordance with at least one technical parameter limitation.

17. The system of claim 1 wherein the determining of the at least one region of interest comprises identifying a position of at least one of an anatomical feature, a radio-opaque marker, and a fluorescent marker, and, based at least partly on the identified position, delineating a target volume for treatment, the region of interest comprising the delineated target volume.

18. A method for automatically planning a radiation therapy treatment and delivering the radiation therapy treatment using a radiation therapy treatment system, the method comprising;
at a processor:
determining at least one region of interest for the radiation therapy treatment;
using at least one clinical requirement to be met for the radiation therapy treatment where the at least one clinical requirement is applied to the at least one region of interest, calculating at least one current technical parameter that controls a technical operation of the radiation therapy treatment system to satisfy the at least one clinical requirement using a predefined empirical relationship, the predefined empirical relationship comprising a previous technical parameter from a previously used radiation therapy treatment plan; and
generating a treatment plan comprising a set of technical parameters, including the at least one calculated current technical parameter, for the radiation therapy treatment for delivery using the radiation therapy treatment system; and
delivering the radiation therapy treatment according to the generated treatment plan using the radiation therapy treatment system.

19. The method of claim 18, wherein the calculating of the at least one current technical parameter comprises using at least one optimization parameter determined from the predefined empirical relationship.

20. The method of claim 19 wherein the determined optimization parameter comprises an empirical value obtained from a lookup table.

21. The method of claim 20 wherein the lookup table contains empirical values determined from a plurality of previously used treatment plans.

22. The method of claim 19 wherein the optimization parameter is one of: a segment number, a segment area, a maximum lung distance value, and an average lung distance value.

23. The method of claim 18 wherein the determining of the at least one region of interest comprises identifying a position of at least one marker, and based at least partly on the identified marker position delineating a target volume for treatment, the region of interest comprising the delineated target volume.

24. The method of claim 23 wherein the calculating of the at least one current technical parameter is based at least partly on the identified position of the at least one marker.

25. The method of claim 23 wherein the at least one marker comprises at least one of an anatomical feature, a radio-opaque marker, and a fluorescent marker.

26. The method of claim 18 wherein the at least one region of interest is determined using an imaging modality selected from: magnetic resonance (MR), computer tomography (CT), cone-beam CT (CBCT), and positron emission tomography (PET).

27. The method of claim 18 wherein the at least one current technical parameter comprises at least one of: a gantry angle, a collimator angle, a collimator jaw setting, a treatment beam isocenter, and a treatment beam strength.

28. The method of claim 18 further comprising displaying a user interface for inputting a user-specified clinical requirement.

29. The method of claim 28 wherein the user interface provides at least one default setting.

30. The method of claim 18 wherein the radiation therapy is for treatment of breast tissue.

31. The method of claim 18 wherein the at least one clinical requirement is one of:
specification of allowable non-target tissue in treatment field;
specification of margin of coverage of target tissue;
prioritization of coverage of target tissue;
prioritization of avoidance of non-target tissue; and
restriction of adjustments for one or more technical parameters in the set of technical parameters.

32. The method of claim 18 wherein:
the determining of the at least one region of interest comprises identifying a position of at least one marker, and based at least partly on the identified marker position delineating a volume for treatment, the region of interest comprising the delineated volume; and
the method further comprises:
calculating a generated treatment field based at least partly on the calculated at least one current technical parameter;
identifying an avoid volume of the delineated volume within the calculated generated treatment field; and
repeatedly adjusting the at least one current technical parameter, and correspondingly re-calculating the generated treatment field and re-identifying the avoid volume based at least partly on the respectively adjusted at least one current technical parameter until the avoid volume is optimized at least partly in accordance with at least one optimization parameter determined from the empirical relationship.

33. The method of claim 32 wherein the at least one optimization parameter comprises minimization of the avoid volume.

34. The method of claim 32 wherein the avoid volume is optimized at least partly in accordance with at least one technical parameter limitation.

* * * * *